(12) United States Patent
Liu et al.

(10) Patent No.: US 11,767,286 B2
(45) Date of Patent: Sep. 26, 2023

(54) PHENYLPROPIONATE COMPOUND, PREPARATION METHOD FOR SAME, AND APPLICATIONS THEREOF

(71) Applicant: SUZHOU PHARMAVAN CO., LTD, Suzhou (CN)

(72) Inventors: Qian Liu, Suzhou (CN); Yunsen Li, Suzhou (CN); Shiping Deng, Suzhou (CN); Yuan Gao, Suzhou (CN); Shanning Lou, Suzhou (CN); Yunhui Yu, Suzhou (CN); Chuanliang Jiang, Suzhou (CN)

(73) Assignee: SUZHOU PHARMAVAN CO., LTD, Suzhou (CN)

( * ) Notice: Subject to any disclaimer, the term of this patent is extended or adjusted under 35 U.S.C. 154(b) by 224 days.

(21) Appl. No.: 16/959,186

(22) PCT Filed: Jan. 19, 2018

(86) PCT No.: PCT/CN2018/073357
§ 371 (c)(1),
(2) Date: Jun. 30, 2020

(87) PCT Pub. No.: WO2019/127746
PCT Pub. Date: Jul. 4, 2019

(65) Prior Publication Data
US 2020/0331842 A1 Oct. 22, 2020

(30) Foreign Application Priority Data
Dec. 30, 2017 (CN) .......................... 201711481470.4

(51) Int. Cl.
*C07C 69/734* (2006.01)

(52) U.S. Cl.
CPC ........ *C07C 69/734* (2013.01); *C07B 2200/07* (2013.01)

(58) Field of Classification Search
CPC ... A61P 9/10; C07B 2200/07; C07C 2602/42; C07C 67/303; C07C 67/343; C07C 69/734; C07C 69/736
See application file for complete search history.

(56) References Cited

FOREIGN PATENT DOCUMENTS

| | | |
|---|---|---|
| CN | 1583710 A | 2/2005 |
| CN | 1868998 A | 11/2006 |
| CN | 101239053 A | 8/2008 |
| CN | 102432468 A | 5/2012 |
| CN | 103232347 A | 8/2013 |
| CN | 103570546 A | 2/2014 |
| CN | 104856983 A | 8/2015 |
| EP | 2019090 A1 | 1/2009 |
| JP | 2009537462 A | 10/2009 |
| WO | 2007131446 A1 | 11/2007 |
| WO | 2016179932 A1 | 11/2016 |

OTHER PUBLICATIONS

Extended European Search Report issued in counterpart EP Application No. 18896468.8 dated Oct. 4, 2021 (seven (7) pages).
Riley J. P.: "391. The spectrophotometric determination of the hydroxyl contents of aliphatic and alicyclic alcohols", Journal of The Chemical Society, Jan. 1, 1952 (Jan. 1, 1952), p. 2108, p. 2110; example 9; table I.
Japanese-language Office Action issued in counterpart JP Application No. 2020-524361 dated Mar. 26, 2021 with English translation (ten (10) pages).
Liu, Duan et al. 2010 "Metabolism of Tanshinol Borneol Ester in Rat and Human Liver Microsomes." Drug Metabolism and Disposition. vol. 38, No. 9.
Matsubara, Eri et al. 2011. "(-)-Bornyl acetate induces autonomic relaxation and reduces arousal level after visual display terminal work without any influences of task performance in low-dose condition." Biomedical Research, vol. 32(2), p. 151-157.
Chinese language International Search Report and Written Opinion issued in counterpad PCT Application No. PCT/CN2018/073357 dated Sep. 28, 2018 with English translation (nine (9) pages).
Glaser, Jan et al. 2014. "Antileishmanial Lead Structures from Nature: Analysis of Structure-Activity Relationships of a Compound Library Derived from Caffeic Acid Bornyl Ester". Molecules, vol. 19, p. 1394-1410.

*Primary Examiner* — Lezah Roberts
(74) *Attorney, Agent, or Firm* — David S. Bradin; Maynard Nexsen PC

(57) ABSTRACT

Provided in the present invention are a phenylpropionate compound, a preparation method for same, and applications. The phenylpropionate compound has the structure as represented by formula I. The phenylpropionate compound of the present invention, a pharmaceutically acceptable salt, a solvate, a prodrug, and a tautomer or stereochemical isomer or pharmaceutical composition of the compound provide improved anti-inflammatory and antiplatelet effects and, at the same time, provide an extended time window for treatment, are free of obvious side effects, safe and effective, applicable in an antithrombus, anti-inflammatory, and cerebral stroke treating medicament, and have broad application prospects.

14 Claims, 4 Drawing Sheets

PHENYLPROPIONATE COMPOUND, PREPARATION METHOD FOR SAME, AND APPLICATIONS THEREOF

CROSS REFERENCE TO RELATED APPLICATIONS

This application is a 35 U.S.C. § 371 U.S. national phase entry of International Application No. PCT/CN2018/073357 having an international filing date of Jan. 19, 2018, which claims the benefit of Chinese Application No. 201711481470.4 filed Dec. 30, 2017, each of which is incorporated herein by reference in its entirety.

TECHNICAL FIELD

The present disclosure belongs to the field of chemical medicines and relates to a phenylpropionate compound, and a preparation method and use thereof.

BACKGROUND

Cerebral stroke is a disease involving brain tissue damages due to obstruction of blood circulation caused by a sudden rupture of a cerebral vessel or a blockage in a vessel. Ischemic stroke refers to necrosis of local brain tissues including nerve cells, glial cells, and vessels due to insufficient blood supply.

*Report on Cardiovascular Diseases in China* (2013) shows that the incidence of cerebrovascular diseases in China is on the rise. The Global Burden of Disease Study 2010 reports that cerebral stroke is the third factor affecting disability-adjusted life years (DALYs). Meanwhile, cerebral stroke is the second cause of death for people over 60, and is one of the most fatal neurological diseases. In China, cerebral stroke has become the main cause of death. Cerebral stroke is characterized by high incidence, a high recurrence rate, a high disability rate, and a high mortality rate.

In China, 1.5 million people die of cerebral stroke and about 2 million people develop cerebral stroke every year. Someone develops cerebral stroke every 12 seconds and someone dies of cerebral stroke every 21 seconds on average. The mortality rate of cerebral stroke in China is 4-5 times higher than that in European and American countries, 3.5 times higher than that in Japan, and even higher than that in developing countries such as India and Thailand.

Three quarters of stroke patients suffer from different levels of disabilities and one quarter of stroke patients suffer from severe disabilities after cured, which is embodied as follows: about ¾ of stroke patients have limb dysfunction, about ⅔ of stroke patients have cognitive dysfunction (half are dementia) and about ½ of stroke patients have depression. Medical expenses of cerebral stroke bring a serious burden to the society and families, and the disability brings great pains and serious inconvenience to stroke patients and their families in spirit and life.

Ischemic stroke, as the name implies, is a disease caused by the interrupted oxygen supply after cerebral ischemia. Interruption of oxygen supply to brain tissues will immediately causes energy depletion in nerve cells, lactic acid accumulation as a result of glycolysis, destruction in ion homeostasis inside and outside the cells, abnormal release of neurotransmitters, toxic effects by nitric oxide and excitatory amino acids, and further damage to brain cells by oxygen free radicals and inflammatory factors after reperfusion. These pathological and biochemical changes happen one after another, resulting in a waterfall effect.

The treatment of acute ischemic stroke focuses on the following two links: improving and restoring blood supply to ischemia-damaged brain tissues as soon as possible and protecting brain tissues from further damages by metabolic toxicants. The most fundamental treatment measure is to break up blood clots at an early stage to unblock blocked vessels, so as to provide a timely blood supply to hypoxic brain tissues before irreversible damages, suppress a series of chain reactions of chemical signaling factors that damage neurons, and increase the tolerance of brain tissues, thereby rescuing functions of brain tissues in penumbras.

However, a time window has to be considered in the treatment of cerebral stroke, especially ischemic cerebral stroke. That is, a certain treatment used for reducing the degree of brain damages, promoting functional recovery, and improving a long-term prognosis takes effect only within a limited time period after a cerebral stroke attack. The time window for treating an ischemic cerebrovascular disease is preferably 1-3 h and should be no more than 6 h in principle. Random control trials show that intravenous administration of a recombinant tissue-type plasminogen activator (rt-PA) to an ischemic stroke patient within 3 h after an attack is a very effective treatment. Such treatment relies on salvageable penumbras to exhibit its clinical benefits. However, only less than 5% of patients received treatment within the time window. Due to the limitation of the time window, few patients received an rt-PA thrombolytic therapy. In addition, rt-PA has a certain risk of intracranial hemorrhage, which also limits the clinical application of rt-PA to a certain degree.

Blood-brain barrier exists between brain cells and plasma which is formed by cerebral capillary walls and neuroglia cells, and between cerebrospinal fluid and plasma which is formed by choroid plexus. The barrier can prevent the passage of some substances from blood into brain tissues. In a process of using a medicament for treating cerebral stroke, the medicament needs to penetrate through the blood-brain barrier and reach an effective concentration to take effect. However, most medicament molecules cannot penetrate through the blood-brain barrier into the brain. Therefore, many medicaments for treating brain diseases cannot play an ideal pharmacodynamic effect in animal trials though they can demonstrate good medicament-target binding activity in in vitro trials.

Therefore, it is still an urgent problem to be solved in clinical to find a safe and effective medicament for treating cerebral stroke, which is readily penetrate through the blood-brain barrier into the brain to exert good anti-inflammatory and anti-platelet, etc. effects and has an extended treatment time window.

SUMMARY

In view the deficiencies in the prior art, an object of the present disclosure is to provide a phenylpropionate compound, and a pharmaceutically acceptable salt, solvate, prodrug, tautomer or stereochemical isomer thereof, and a preparation method and use thereof.

To achieve the object, the present disclosure adopts the technical solutions described below.

In an aspect, the present disclosure provides a phenylpropionate compound which has a structure represented by Formula I:

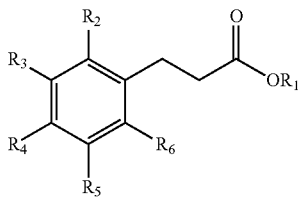

Formula I wherein R₁ is (1R,2S,4R)-1,7,7-trimethylbicyclo[2.2.1]heptan-2-yl or (1S,2R,4S)-1,7,7-trimethylbicyclo[2.2.1]heptan-2-yl, $R_2$, $R_3$, $R_4$, $R_5$, and $R_6$ are each independently hydrogen, halogen, nitro, amino, hydroxy, substituted or unsubstituted linear alkyl, substituted or unsubstituted branched alkyl, substituted or unsubstituted alkoxy, or substituted or unsubstituted alkylamino, and not all of $R_2$, $R_3$, $R_4$, $R_5$, and $R_6$ are hydrogen.

Preferably, $R_2$, $R_3$, $R_4$, $R_5$, and $R_6$ are each independently any one of hydrogen, fluorine, chlorine, bromine, nitro, amino, methyl, trifluoromethyl, ethyl, n-propyl, isopropyl, hydroxy, methoxy, trifluoromethoxy, ethoxy, methylamino, dimethylamino, ethylamino, or diethylamino, and not all of $R_2$, $R_3$, $R_4$, $R_5$, and $R_6$ are hydrogen.

In a preferred embodiment of the present disclosure, $R_2$ is hydrogen, methyl, or fluorine.

In a preferred embodiment of the present disclosure, $R_3$ is hydroxy, methoxy, or trifluoromethoxy.

In a preferred embodiment of the present disclosure, $R_4$ is hydroxy or methoxy.

In a preferred embodiment of the present disclosure, $R_5$ is hydrogen, fluorine, hydroxy, methoxy, methyl, or amino.

In a preferred embodiment of the present disclosure, $R_6$ is hydrogen or bromine.

Preferably, the phenylpropionate compound is any one or a combination of at least two of compounds having the following Formulas A to E:

Formula A

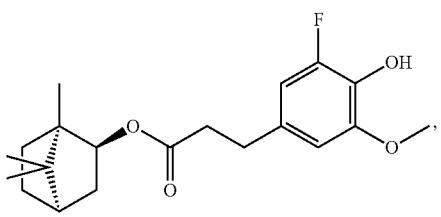

Formula B

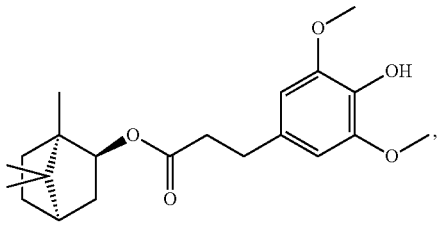

Formula C

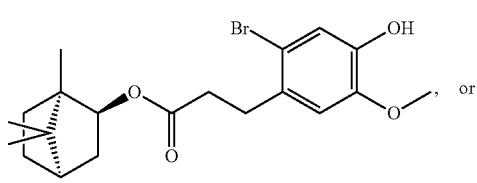

Formula D

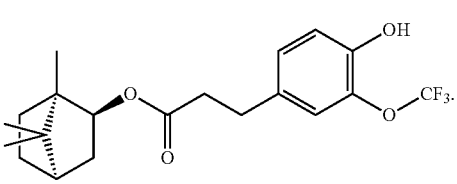

Formula E

A second object of the present disclosure is to provide a preparation method for the phenylpropionate compound described above, which is:

hydrogenating a phenylacrylate compound represented by Formula IV in the presence of a catalyst to obtain a phenylpropionate compound represented by Formula I, with a reaction equation as follows:

Formula IV

Formula I wherein R₁ is (1R,2S,4R)-1,7,7-trimethylbicyclo[2.2.1]heptan-2-yl or (1R,2S,4S)-1,7,7-trimethylbicyclo[2.2.1]heptan-2-yl, $R_2$, $R_3$, $R_4$, $R_5$, and $R_6$ are each independently hydrogen, halogen, nitro, amino, hydroxy, substituted or unsubstituted linear alkyl, substituted or unsubstituted branched alkyl, substituted or unsubstituted alkoxy, or substituted or unsubstituted alkylamino, and not all of $R_2$, $R_3$, $R_4$, $R_5$, and $R_6$ are hydrogen.

Preferably, a molar ratio of the phenylacrylate compound represented by Formula IV to the catalyst is 1:(0.05-1.0), for example, 1:0.05, 1:0.08, 1:0.1, 1:0.3, 1:0.5, 1:0.8, or 1:1.

Preferably, the catalyst is any one or a combination of at least two of Raney nickel, nickel boride, palladium carbon, platinum carbon, cuprous chromate, chlorotris(triphenylphosphine)rhodium, chlorohydridotris(triphenylphosphine)ruthenium, or hydridotris(triphenylphosphine) iridium.

Preferably, a reductant in the hydrogenation reaction is hydrogen or ammonium formate.

Preferably, a molar ratio of the reductant to the phenylacrylate compound represented by Formula IV is (15-25):1, for example, 15:1, 16:1, 17:1, 18:1, 19:1, 20:1, 21:1, 22:1, 23:1, 24:1, or 25:1.

Preferably, the reaction is performed at a temperature of 0 to 80° C., for example, 0° C., 5° C., 10° C., 15° C., 20° C., 25° C., 30° C., 35° C., 40° C., 50° C., 60° C., 70° C., or 80° C.

Preferably, the reaction is performed for 1-30 h, for example, 1 h, 5 h, 8 h, 10 h, 13 h, 15 h, 18 h, 20 h, 22 h, 25 h, 28 h, or 30 h.

In the present disclosure, the phenylacrylate compound represented by Formula IV may be prepared by various methods. For example, one preparation method may be: reacting a malonate monoester represented by Formula II with a benzaldehyde compound represented by Formula III in the presence of a catalyst to obtain a phenylacrylate compound represented by Formula I, with a reaction equation as follows:

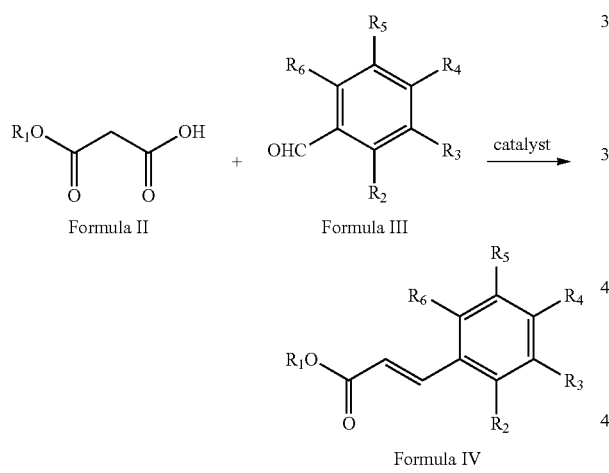

Formula II    Formula III

Formula IV wherein $R_1$ is (1R,2S,4R)-1,7,7-trimethylbicyclo[2.2.1]heptan-2-yl or (1S,2R,4S)-1,7,7-trimethylbicyclo[2.2.1]heptan-2-yl, $R_2$, $R_3$, $R_4$, $R_5$, and $R_6$ are each independently hydrogen, halogen, nitro, amino, hydroxy, substituted or unsubstituted linear alkyl, substituted or unsubstituted branched alkyl, substituted or unsubstituted alkoxy, or substituted or unsubstituted alkylamino, and not all of $R_2$, $R_3$, $R_4$, $R_5$, and $R_6$ are hydrogen.

Preferably, a molar ratio of the malonate monoester represented by Formula II to the benzaldehyde compound represented by Formula III is (0.5-1.5):1, for example, 0.5:1, 0.6:1, 0.7:1, 0.8:1, 0.9:1, 1:1, 1.1:1, 1.2:1, 1.3:1, 1.4:1, or 1.5:1.

Preferably, the catalyst is any one or a combination of at least two of pyridine, piperidine, or acetic acid.

Preferably, the catalyst is used in an amount of 0.1-5 times a molar amount of the substituted benzaldehyde represented by Formula III, for example, 0.1 times, 0.5 times, 0.8 times, 1 time, 2 times, 3 times, 4 times, or 5 times.

Preferably, a solvent of the reaction is any one or a combination of at least two of toluene, xylene, benzene, DMF, n-heptane, or DMSO.

Preferably, the reaction is performed at a temperature of 50 to 150° C., for example, 50° C., 60° C., 70° C., 80° C., 90° C., 100° C., 110° C., 120° C., 130° C., 140° C., or 150° C.

Preferably, the reaction is performed for 1-10 h, for example, 1 h, 1.5 h, 2 h, 2.5 h, 3 h, 4 h, 5 h, 6 h, 7 h, 8 h, 9 h, or 10 h.

In the present disclosure, another preparation method for the phenylacrylate compound represented by Formula IV is: subjecting an alcohol represented by Formula V and a phenylacrylic acid compound represented by Formula VI to a condensation reaction to obtain a phenylacrylate compound represented by Formula IV, with a reaction equation as follows:

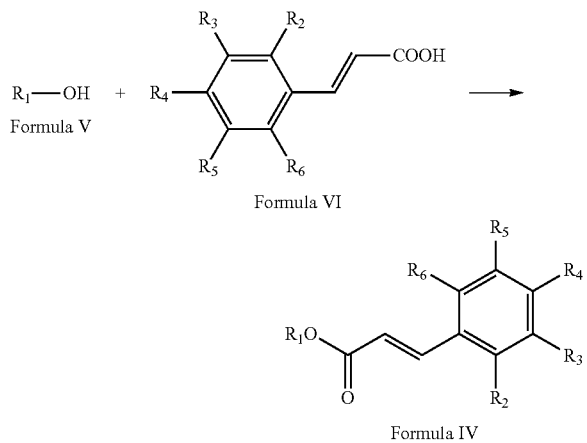

wherein $R_1$ is (1R,2S,4R)-1,7,7-trimethylbicyclo[2.2.1]heptan-2-yl or (1S,2R,4S)-1,7,7-trimethylbicyclo[2.2.1]heptan-2-yl, $R_2$, $R_3$, $R_4$, $R_5$, and $R_6$ are each independently hydrogen, halogen, nitro, amino, hydroxy, substituted or unsubstituted linear alkyl, substituted or unsubstituted branched alkyl, substituted or unsubstituted alkoxy, or substituted or unsubstituted alkylamino, and not all of $R_2$, $R_3$, $R_4$, $R_5$, and $R_6$ are hydrogen.

Preferably, a molar ratio of the alcohol represented by Formula V to the phenylacrylic acid compound represented by Formula VI is (1-1.5):1, for example, 1:1, 1.1:1, 1.2:1, 1.3:1, 1.4:1, or 1.5:1.

Preferably, a solvent of the reaction is any one or a combination of at least two of toluene, xylene, dichloromethane, or trichloromethane.

Preferably, the reaction is performed at a temperature of 15 to 80° C., for example, 15° C., 25° C., 35° C., 45° C., 55° C., 65° C., 75° C., or 80° C.

Preferably, the reaction is performed for 3-30 h, for example, 3 h, 5 h, 8 h, 10 h, 12 h, 15 h, 18 h, 20 h, 22 h, 24 h, 26 h, 28 h, or 30 h.

In the present disclosure, when the phenylacrylic acid compound represented by Formula VI includes other group(s), besides the carboxyl of the acrylic acid, that might react with the alcohol represented by Formula V or the carboxyl on the phenylacrylic acid compound represented by Formula VI, the functional group(s) on the phenylacrylic acid compound represented by Formula VI may be selectively protected by a method known in the art before reacted with the alcohol represented by Formula V, and after the reaction with the alcohol represented by Formula V, protective group(s) is(are) then removed through a known deprotection reaction. For example, when a hydroxy group is included on the benzene ring of the phenylacrylic acid compound represented by Formula VI, it may be protected with a benzyl group, and then reacted with an alcohol represented by Formula V to obtain a product, which is debenzylated to obtain a target product.

In the present disclosure, another preparation method for the phenylacrylate compound represented by Formula IV is: subjecting a compound represented by Formula VII and a benzaldehyde compound represented by Formula III to a Wittig reaction in the presence of a base to obtain a phenylacrylate compound represented by Formula IV, with a reaction equation as follows:

wherein $R_1$ is (1R,2S,4R)-1,7,7-trimethylbicyclo[2.2.1]heptan-2-yl or (1S,2R,4S)-1,7,7-trimethylbicyclo[2.2.1]heptan-2-yl; $R_2$, $R_3$, $R_4$, $R_5$, and $R_6$ are each independently hydrogen, halogen, nitro, amino, hydroxy, substituted or unsubstituted linear alkyl, substituted or unsubstituted branched alkyl, substituted or unsubstituted alkoxy, or substituted or unsubstituted alkylamino, and not all of $R_2$, $R_3$, $R_4$, $R_5$, and $R_6$ are hydrogen; R is diphenyloxyphosphono, diethoxyphosphono, triphenylphosphine bromide, or triphenylphosphine chloride.

Preferably, a molar ratio of the compound represented by Formula VII to the benzaldehyde compound represented by Formula III is 1:(1-1.5), for example, 1:1, 1:1.1, 1:1.2, 1:1.3, 1:1.4, or 1:1.5.

Preferably, the base is any one or a combination of at least two of n-butyl lithium, potassium t-butoxide, sodium methoxide, sodium ethoxide, sodium hydride, or potassium carbonate.

Preferably, the Wittig reaction is performed at a temperature of −80 to 60° C., for example, −80° C., −60° C., −40° C., −20° C., 0° C., 10° C., 20° C., 30° C., 40° C., 50° C., or 60° C.

Preferably, the Wittig reaction is performed for 1-12 h, for example, 1 h, 2 h, 3 h, 4 h, 5 h, 6 h, 7 h, 8 h, 9 h, 10 h, 11 h, or 12 h.

In the present disclosure, the compound represented by Formula VII may be prepared by a method known in the art. For example, (1R,2S,4R)-1,7,7-trimethylbicyclo[2.2.1]heptan-2-ol or (1S,2R,4S)-1,7,7-trimethylbicyclo[2.2.1]heptan-2-ol reacts with a haloacetyl halide in the presence of a base to obtain a haloacetyl ester, which reacts with an organophosphorus reagent to generate a Wittig phosphorus reagent, that is, the compound represented by Formula VII, with a reaction equation as follows:

A fifth object of the present disclosure is to provide a pharmaceutically acceptable salt of the phenylpropionate compound described above.

In the present disclosure, the pharmaceutically acceptable salt is a metal salt of the phenylpropionate compound.

Preferably, the metal salt is selected from a lithium salt, a sodium salt, a potassium salt, or a magnesium salt.

Preferably, the metal salt is selected from a sodium salt or a potassium salt.

A sixth object of the present disclosure is to provide a solvate of the phenylpropionate compound described above.

Preferably, the solvate is a hydrate and/or an alcoholate of the phenylpropionate compound. In the present disclosure, the solvate of the phenylpropionate compound has comparable effects as the phenylpropionate compound.

A seventh object of the present disclosure is to provide a prodrug of the phenylpropionate compound described above.

In the present disclosure, the prodrug refers to a compound that is obtained after a drug is subjected to chemical structure modification, and is inactive or less active in vitro, and releases an active drug through an enzymatic or non-enzymatic conversion in vivo to exert effects.

In the present disclosure, the prodrug of the phenylpropionate compound is inactive or less active in vitro and releases an active phenylpropionate compound after undergoing metabolic changes in vivo, thereby exerting effects.

An eighth object of the present disclosure is to provide a tautomer or a stereochemical isomer of the phenylpropionate compound described above.

In the present disclosure, the tautomer refers to cis- and trans-isomerization of the double bond in the chemical structure, and the stereochemical isomer refers to isomerization of each chiral center in the R1 group.

A ninth object of the present disclosure is to provide a pharmaceutical composition including the phenylpropionate compound described above.

Preferably, the pharmaceutical composition further includes a pharmaceutically acceptable adjuvant.

Preferably, the pharmaceutically acceptable adjuvant is any one or a combination of at least two of an excipient, a diluent, a carrier, a flavoring agent, a binder, or a filler.

Preferably, the pharmaceutical composition is in a dosage form of an oral preparation, a parenteral preparation, or a topical preparation.

For example, in the present disclosure, the pharmaceutical composition may be prepared into solid, semi-solid, liquid, or gas preparations, such as tablets, pills, capsules, powders, granules, ointments, emulsions, suspensions, suppositories, injections, inhalations, gels, microspheres, and aerosols.

A typical routine for administering the compound of the present application or a pharmaceutically acceptable salt thereof or a pharmaceutical composition thereof includes, but is not limited to, oral, rectal, topical, inhalation, parenteral, sublingual, intravaginal, intranasal, intraocular, intraperitoneal, intramuscular, subcutaneous, or intravenous administration.

A tenth object of the present disclosure is to provide use of the phenylpropionate compound described above, the pharmaceutically acceptable salt, the solvate, the prodrug, the tautomer, or the stereochemical isomer thereof, or the pharmaceutical composition in the preparation of a medicament for treating cerebral stroke.

The phenylpropionate compound of the present disclosure, and the pharmaceutically acceptable salt, the solvate, the prodrug, the tautomer, or the stereochemical isomer thereof, or the pharmaceutical composition provides an extended treatment time window, is useful as an anti-thrombus, anti-inflammatory, and cerebral stroke-treating medicament, and shows no obvious side effects.

Compared with the existing art, the present disclosure has beneficial effects described below.

The phenylpropionate compound of the present disclosure, and the pharmaceutically acceptable salt, the solvate, the prodrug, the tautomer, or the stereochemical isomer thereof, or the pharmaceutical composition shows good anti-inflammatory and anti-platelet, etc. effects and provides an extended treatment time window, and shows no obvious side effects, and is safe and effective, and is useful as an anti-thrombus, anti-inflammatory, and cerebral stroke-treating medicament. The compound of the present disclosure is more readily and rapidly distributed into the brain to exert therapeutic effects, and has more clinical significance for cerebral stroke that requires first aid, and has a broad application prospect.

BRIEF DESCRIPTION OF DRAWINGS

wherein Nos. in FIGS. 2 to 4 represent the No. of a trial animal, and brain slices are divided into six slices from top to bottom.

DETAILED DESCRIPTION

Figure 1:
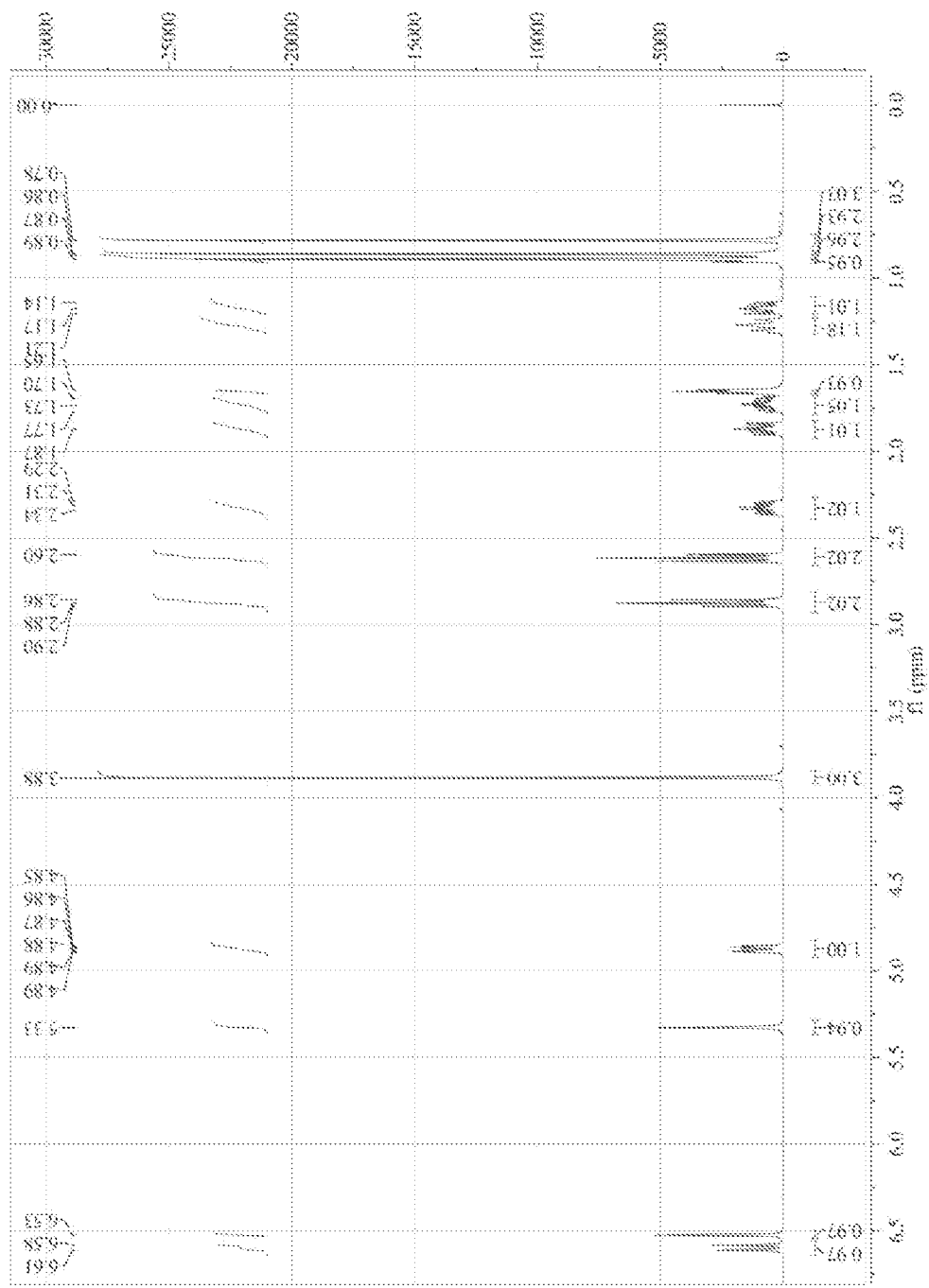
FIG. 1 is an H NMR spectrum of Compound A of the present disclosure.

The technical solutions of the present disclosure are further described below through specific examples. Those skilled in the art should understand that the examples described herein are merely used for a better understanding of the present disclosure and should not be construed as specific limitations to the present disclosure.

Example 1 Synthesis of a Compound of Formula A (1) Under nitrogen protection, mono(1R,2S,4R)-1,7,7-trimethylbicyclo[2.2.1]heptan-2-ol malonate (11.5 g, 47.9 mmol) and 3-fluoro-4-hydroxy-5-methoxybenzaldehyde (7.3 g, 42.9 mmol) were added to toluene (100 ml), and pyridine (7.6 g, 95.8 mmol) and piperidine (0.4 g, 4.7 mmol) were added. The mixture was warmed to 120° C. and reacted for 5 h. After the reaction was completed, the reaction solution was cooled, washed with a 1N hydrochloric acid solution, a saturated NaHCO₃ solution, and a saturated NaCl solution, dried with anhydrous sodium sulfate for 4 h, and concentrated to dryness. The residue was recrystallized from ethyl acetate/petroleum ether to obtain 10.2 g of (1R,2S,4R)-1,7,7-trimethylbicyclo[2.2.1]heptan-2-yl (E)-3-(3-fluoro-4-hydroxy-5-methoxyphenyl)acrylate as a white powder solid with a yield of 68.5%. EI-MS M/Z 349.2[M⁺], 347.3[M⁻].

¹H-NMR (CDCl₃, 500 MHz) 0.78 (3H, s, H-12), 0.86, 0.87 (each 3H, s, H-13, 14), 0.89 (1H, d, H-8α), 1.14 (1H, m, H-10β), 1.17~1.21 (1H, t, H-11α), 1.65 (1H, t, H-9), 1.70~1.76 (1H, m, H-10α), 1.86 (1H, m, H-11β), 2.29~2.33 (1H, m, H-8β), 2.60 (2H, t, H-5), 2.88 (2H, t, H-6), 3.88 (3H, s, H-2), 4.85~4.89 (1H, dd, H-7), 5.33 (1H, s, H-3), 6.53 (1H, s, H-1), 6.58~6.61 (1H, d, H-4). The H NMR spectrum is shown in FIG. 1.

(2) At room temperature, (1R,2S,4R)-1,7,7-trimethylbicyclo[2.2.1]heptan-2-yl (E)-3-(3-fluoro-4-hydroxy-5-methoxyphenyl)acrylate (1.0 g, 2.9 mmol) was added to methanol (20 ml), 10% palladium carbon (0.1 g) was added, and then ammonium formate (3.6 g, 57.1 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.95 g of white powder with a yield of 94.4%. EI-MS M/Z 351.1 [M⁺], 349.3 [M⁻].

Example 2 Synthesis of a Compound of Formula A (1) Under nitrogen protection, mono(1R,2S,4R)-1,7,7-trimethylbicyclo[2.2.1]heptan-2-ol malonate (5.3 g, 22.1 mmol) and 3-fluoro-4-hydroxy-5-methoxybenzaldehyde (3.0 g, 17.6 mmol) were added to toluene (50 ml), and piperidine (0.38 g, 4.4 mmol) and acetic acid (0.26 g, 4.4 mmol) were added. The mixture was warmed to 120° C. and reacted for 5 h. After the reaction was completed, the reaction solution was cooled, washed with a 1N hydrochloric acid solution, a saturated NaHCO₃ solution, and a saturated NaCl solution, dried with anhydrous sodium sulfate for 4 h, and concentrated to dryness. The residue was recrystallized from ethyl acetate/petroleum ether to obtain 4.3 g of (1R,2S,4R)-1,7,7-trimethylbicyclo[2.2.1]heptan-2-yl (E)-3-(3-fluoro-4-hydroxy-5-methoxyphenyl)acrylate as a white powder solid with a yield of 70.5%.

(2) At room temperature, (1R,2S,4R)-1,7,7-trimethylbicyclo[2.2.1]heptan-2-yl (E)-3-(3-fluoro-4-hydroxy-5-methoxyphenyl)acrylate (1.0 g, 2.9 mmol) was added to methanol (20 ml), 10% palladium carbon (0.1 g) was added, and then ammonium formate (2.7 g, 43.5 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.92 g of white powder with a yield of 91.4%. EI-MS M/Z 351.1[M⁺], 349.3 [M⁻].

Example 3 Synthesis of a Compound of Formula B (1) Under nitrogen protection, mono(1R,2S,4R)-1,7,7-trimethylbicyclo[2.2.1]heptan-2-ol malonate (11.5 g, 47.9 mmol) and 3,4-dihydroxy-5-methoxybenzaldehyde (7.2 g, 42.9 mmol) were added to toluene (100 ml), and pyridine (7.6 g, 95.8 mmol) and piperidine (0.4 g, 4.7 mmol) were added. The mixture was warmed to 120° C. and reacted for 5 h. After the reaction was completed, the reaction solution was cooled, washed with a 1N hydrochloric acid solution, a saturated NaHCO$_3$ solution, and a saturated NaCl solution, dried with anhydrous sodium sulfate for 4 h, and concentrated to dryness. The residue was recrystallized from ethyl acetate/petroleum ether to obtain 8.3 g of (1R,2S,4R)-1,7,7-trimethylbicyclo[2.2.1]heptan-2-yl (E)-3-(3,4-hydroxy-5-methoxyphenyl)acrylate as a white powder solid with a yield of 55.8%. EI-MS M/Z 347.2[M$^+$], 345.2[M$^-$].

(2) At room temperature, (1R,2S,4R)-1,7,7-trimethylbicyclo[2.2.1]heptan-2-yl (E)-3-(3,4-hydroxy-5-methoxyphenyl)acrylate (1.0 g, 2.9 mmol) was added to methanol (20 ml), 10% palladium carbon (0.1 g) was added, and then ammonium formate (3.6 g, 57.1 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.95 g of white powder with a yield of 94.5%. EI-MS M/Z 349.2[M$^+$], 347.2[M$^-$].

Example 4 Synthesis of a Compound of Formula B (1) Under nitrogen protection, mono(1R,2S,4R)-1,7,7-trimethylbicyclo[2.2.1]heptan-2-ol malonate (5.3 g, 22.1 mmol) and 3,4-dihydroxy-5-methoxybenzaldehyde (2.9 g, 17.6 mmol) were added to toluene (50 ml), and piperidine (0.38 g, 4.4 mmol) and acetic acid (0.26 g, 4.4 mmol) were added. The mixture was warmed to 120° C. and reacted for 5 h. After the reaction was completed, the reaction solution was cooled, washed with a 1N hydrochloric acid solution, a saturated NaHCO$_3$ solution, and a saturated NaCl solution, dried with anhydrous sodium sulfate for 4 h, and concentrated to dryness. The residue was recrystallized from ethyl acetate/petroleum ether to obtain 3.6 g of (1R,2S,4R)-1,7,7-trimethylbicyclo[2.2.1]heptan-2-yl (E)-3-(3,4-hydroxy-5-methoxyphenyl)acrylate as a white powder solid with a yield of 59.1%.

(2) At room temperature, (1R,2S,4R)-1,7,7-trimethylbicyclo[2.2.1]heptan-2-yl (E)-3-(3,4-hydroxy-5-methoxyphenyl)acrylate (1.0 g, 2.9 mmol) was added to methanol (20 ml), 10% palladium carbon (0.1 g) was added, and then ammonium formate (4.6 g, 72.5 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.97 g of white powder with a yield of 96.5%. EI-MS M/Z 349.2[M$^+$], 347.2[M$^-$].

Example 5 Synthesis of a Compound of Formula C (1) Under nitrogen protection, mono(1R,2S,4R)-1,7,7-trimethylbicyclo[2.2.1]heptan-2-ol malonate (11.5 g, 47.9 mmol) and 4-hydroxy-3,5-dimethoxybenzaldehyde (7.8 g, 42.9 mmol) were added to toluene (100 ml), and pyridine (7.6 g, 95.8 mmol) and piperidine (0.4 g, 4.7 mmol) were added. The mixture was warmed to 120° C. and reacted for 5 h. After the reaction was completed, the reaction solution was cooled, washed with a 1N hydrochloric acid solution, a saturated NaHCO$_3$ solution, and a saturated NaCl solution, dried with anhydrous sodium sulfate for 4 h, and concentrated to dryness. The residue was recrystallized from ethyl acetate/petroleum ether to obtain 8.9 g of (1R,2S,4R)-1,7,7-trimethylbicyclo[2.2.1]heptan-2-yl (E)-3-(4-hydroxy-3,5-dimethoxyphenyl)acrylate as a white powder solid with a yield of 57.6%. EI-MS M/Z 361.2[M$^+$], 359.2[M$^-$].

(2) At room temperature, (1R,2S,4R)-1,7,7-trimethylbicyclo[2.2.1]heptan-2-yl (E)-3-(4-hydroxy-3,5-dimethoxyphenyl)acrylate (1.0 g, 2.8 mmol) was added to methanol (20 ml), 10% palladium carbon (0.1 g) was added, and then ammonium formate (3.6 g, 57.1 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.94 g of white powder with a yield of 93.5%. EI-MS M/Z 363.5[M$^+$], 361.7[M$^-$].

Example 6 Synthesis of a Compound of Formula C (1) Under nitrogen protection, mono(1R,2S,4R)-1,7,7-trimethylbicyclo[2.2.1]heptan-2-ol malonate (5.3 g, 22.1 mmol) and 4-hydroxy-3,5-dimethoxybenzaldehyde (3.2 g, 17.6 mmol) were added to toluene (50 ml), and piperidine (0.38 g, 4.4 mmol) and acetic acid (0.26 g, 4.4 mmol) were added. The mixture was warmed to 120° C. and reacted for 5 h. After the reaction was completed, the reaction solution was cooled, washed with a 1N hydrochloric acid solution, a saturated NaHCO$_3$ solution, and a saturated NaCl solution, dried with anhydrous sodium sulfate for 4 h, and concentrated to dryness. The residue was recrystallized from ethyl acetate/petroleum ether to obtain 3.6 g of (1R,2S,4R)-1,7,7-trimethylbicyclo[2.2.1]heptan-2-yl (E)-3-(4-hydroxy-3,5-dimethoxyphenyl)acrylate as a white powder solid with a yield of 57.1%.

(2) At room temperature, (1R,2S,4R)-1,7,7-trimethylbicyclo[2.2.1]heptan-2-yl (E)-3-(4-hydroxy-3,5-dimethoxyphenyl)acrylate (1.0 g, 2.8 mmol) was added to methanol (20 ml), 10% palladium carbon (0.1 g) was added, and then ammonium formate (4.4 g, 70 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.95 g of white powder with a yield of 94.5%. EI-MS M/Z 363.5[M$^+$], 361.7[M$^-$].

Example 7 Synthesis of a Compound of Formula D (1) Under nitrogen protection, mono(1R,2S,4R)-1,7,7-trimethylbicyclo[2.2.1]heptan-2-ol malonate (11.5 g, 47.9 mmol) and 2-bromo-4-hydroxy-5-methoxybenzaldehyde (9.9 g, 42.9 mmol) were added to toluene (100 ml), and pyridine (7.6 g, 95.8 mmol) and piperidine (0.4 g, 4.7 mmol) were added. The mixture was warmed to 120° C. and reacted for 5 h. After the reaction was completed, the reaction solution was cooled, washed with a 1N hydrochloric acid solution, a saturated NaHCO$_3$ solution, and a saturated NaCl solution, dried with anhydrous sodium sulfate for 4 h, and concentrated to dryness. The residue was recrystallized from ethyl acetate/petroleum ether to obtain 13.6 g of (1R,2S,4R)-1,7,7-trimethylbicyclo[2.2.1]heptan-2-yl (E)-3-(2- bromo-4-hydroxy-5-methoxyphenyl)acrylate as a white powder solid with a yield of 77.4%. EI-MS M/Z 409.1[M⁺], 407.1[M⁻].

(2) At room temperature, (1R,2S,4R)-1,7,7-trimethylbicyclo[2.2.1]heptan-2-yl (E)-3-(2-bromo-4-hydroxy-5-methoxyphenyl)acrylate (1.0 g, 2.4 mmol) was added to methanol (20 ml), 10% palladium carbon (0.1 g) was added, and then ammonium formate (3.6 g, 57.1 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.91 g of white powder with a yield of 90.5%. EI-MS M/Z 411.1[M⁺], 409.3[M⁻].

Example 8 Synthesis of a Compound of Formula D (1) Under nitrogen protection, mono(1R,2S,4R)-1,7,7-trimethylbicyclo[2.2.1]heptan-2-ol malonate (5.3 g, 22.1 mmol) and 2-bromo-4-hydroxy-5-methoxybenzaldehyde (4.1 g, 17.6 mmol) were added to toluene (50 ml), and piperidine (0.38 g, 4.4 mmol) and acetic acid (0.26 g, 4.4 mmol) were added. The mixture was warmed to 120° C. and reacted for 5 h. After the reaction was completed, the reaction solution was cooled, washed with a 1N hydrochloric acid solution, a saturated NaHCO₃ solution, and a saturated NaCl solution, dried with anhydrous sodium sulfate for 4 h, and concentrated to dryness. The residue was recrystallized from ethyl acetate/petroleum ether to obtain 5.9 g of (1R,2S,4R)-1,7,7-trimethylbicyclo[2.2.1]heptan-2-yl (E)-3-(2-bromo-4-hydroxy-5-methoxyphenyl)acrylate as a white powder solid with a yield of 81.9%.

(2) At room temperature, (1R,2S,4R)-1,7,7-trimethylbicyclo[2.2.1]heptan-2-yl (E)-3-(2-bromo-4-hydroxy-5-methoxyphenyl)acrylate (1.0 g, 2.4 mmol) was added to methanol (20 ml), 10% palladium carbon (0.1 g) was added, and then ammonium formate (3.8 g, 60 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.94 g of white powder with a yield of 93.5%. EI-MS M/Z 411.1[M⁺], 409.3[M⁻].

Example 9 Synthesis of a Compound of Formula E (1) Under nitrogen protection, mono(1R,2S,4R)-1,7,7-trimethylbicyclo[2.2.1]heptan-2-ol malonate (11.5 g, 47.9 mmol) and 4-hydroxy-3-trifluoromethoxybenzaldehyde (8.8 g, 42.9 mmol) were added to toluene (100 ml), and pyridine (7.6 g, 95.8 mmol) and piperidine (0.4 g, 4.7 mmol) were added. The mixture was warmed to 120° C. and reacted for 5 h. After the reaction was completed, the reaction solution was cooled, washed with a 1N hydrochloric acid solution, a saturated NaHCO₃ solution, and a saturated NaCl solution, dried with anhydrous sodium sulfate for 4 h, and concentrated to dryness. The residue was recrystallized from ethyl acetate/petroleum ether to obtain 10.5 g of (1R,2S,4R)-1,7,7-trimethylbicyclo[2.2.1]heptan-2-yl (E)-3-(4-hydroxy-3-trifluoromethoxyphenyl)acrylate as a white powder solid with a yield of 64.0%. EI-MS M/Z 385.1[M⁺], 383.1[M⁻].

(2) At room temperature, (1R,2S,4R)-1,7,7-trimethylbicyclo[2.2.1]heptan-2-yl (E)-3-(4-hydroxy-3-trifluoromethoxyphenyl)acrylate (1.0 g, 2.6 mmol) was added to methanol (20 ml), 10% palladium carbon (0.1 g) was added, and then ammonium formate (3.6 g, 57.1 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.96 g of white powder with a yield of 95.5%. EI-MS M/Z 387.2[M⁺], 385.3[M⁻].

Example 10 Synthesis of a Compound of Formula E (1) Under nitrogen protection, mono(1R,2S,4R)-1,7,7-trimethylbicyclo[2.2.1]heptan-2-ol malonate (5.3 g, 22.1 mmol) and 4-hydroxy-3-trifluoromethoxybenzaldehyde (3.6 g, 17.6 mmol) were added to toluene (50 ml), and piperidine (0.38 g, 4.4 mmol) and acetic acid (0.26 g, 4.4 mmol) were added. The mixture was warmed to 120° C. and reacted for 5 h. After the reaction was completed, the reaction solution was cooled, washed with a 1N hydrochloric acid solution, a saturated NaHCO₃ solution, and a saturated NaCl solution, dried with anhydrous sodium sulfate for 4 h, and concentrated to dryness. The residue was recrystallized from ethyl acetate/petroleum ether to obtain 4.7 g of (1R,2S,4R)-1,7,7-trimethylbicyclo[2.2.1]heptan-2-yl (E)-3-(4-hydroxy-3-trifluoromethoxyphenyl)acrylate as a white powder solid with a yield of 69.5%.

(2) At room temperature, (1R,2S,4R)-1,7,7-trimethylbicyclo[2.2.1]heptan-2-yl (E)-3-(4-hydroxy-3-trifluoromethoxyphenyl)acrylate (1.0 g, 2.6 mmol) was added to methanol (20 ml), 10% palladium carbon (0.1 g) was added, and then ammonium formate (2.5 g, 39 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.93 g of white powder with a yield of 92.5%. EI-MS M/Z 387.2[M⁺], 385.3[M⁻].

Example 11 Synthesis of a Compound of Formula A (1) (E)-3-fluoro-4-benzyloxy-5-methoxyphenylacrylic acid (7.8 g, 0.026 mol) was added into dichloromethane (50 ml). The mixture was cooled in an ice-salt bath to 0° C., and dicyclohexylcarbodiimide (5.43 g, 0.026 mol) and 4-dimethylaminopyridine (0.96 g, 0.008 mol) were added. A drying tube was equipped and the mixture was reacted for 1 h. (1R,2S,4R)-1,7,7-trimethylbicyclo[2.2.1]heptan-2-ol (4.1 g, 0.026 mol) was dissolved in dichloromethane (25 ml) and added dropwise to the reaction solution. After dropwise addition, the ice-salt bath was removed, and the reaction was naturally warmed for overnight. After the reaction was completed, solids were filtered, and the filter cake was washed with an appropriate amount of dichloromethane. The filtrate was evaporated to dryness, and the residue was subjected to column chromatography to obtain (1R,2S,4R)-1,7,7-trimethylbicyclo[2.2.1]heptan-2-yl (E)-3-(4-benzyloxy-3-fluoro-5-methoxyphenyl)acrylate (9.8 g).

(1R,2S,4R)-1,7,7-trimethylbicyclo[2.2.1]heptan-2-yl (E)-3-(4-benzyloxy-3-fluoro-5-methoxy phenyl)acrylate (9.2 g, 0.021 mol) was added into tetrahydrofuran (90 ml). The mixture was stirred well, and ammonium formate (6.8 g, 0.105 mol) and palladium carbon (1.8 g, 0.147 mol) were added in sequence. The mixture was reacted for 3 h. After the reaction was completed, palladium carbon was filtered with Celite, and washed with an appropriate amount of tetrahydrofuran. The filtrate was evaporated to dryness. The residue was recrystallized from petroleum ether or isopropanol to obtain 6.1 g of (1R,2S,4R)-1,7,7-trimethylbicyclo [2.2.1]heptan-2-yl (E)-3-(3-fluoro-4-hydroxy-5-methoxyphenyl)acrylate as a white powder solid with a yield of 83.4%.

(2) At room temperature, (1R,2S,4R)-1,7,7-trimethylbicyclo[2.2.1]heptan-2-yl (E)-3-(3-fluoro-4-hydroxy-5-methoxyphenyl)acrylate (1.0 g, 2.9 mmol) was added to methanol (20 ml), 10% palladium carbon (0.1 g) was added, and then ammonium formate (2.7 g, 43.5 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.92 g of white powder with a yield of 91.4%. EI-MS M/Z 351.1[M$^+$], 349.3[M$^-$].

Example 12 Synthesis of a Compound of Formula B (1) (E)-3,4-dibenzyloxy-5-methoxyphenylacrylic acid (10.2 g, 0.026 mol) was added into dichloromethane (50 ml). The mixture was cooled in an ice-salt bath to 0° C., and dicyclohexylcarbodiimide (5.43 g, 0.026 mol) and 4-dimethylaminopyridine (0.96 g, 0.008 mol) were added. A drying tube was equipped and the mixture was reacted for 1 h. (1R,2S,4R)-1,7,7-trimethylbicyclo[2.2.1]heptan-2-ol (4.1 g, 0.026 mol) was dissolved in dichloromethane (25 ml) and added dropwise to the reaction solution. After dropwise addition, the ice-salt bath was removed, and the reaction was naturally warmed for overnight. After the reaction was completed, solids were filtered, and the filter cake was washed with an appropriate amount of dichloromethane. The filtrate was evaporated to dryness, and the residue was subjected to column chromatography to obtain (1R,2S,4R)-1,7,7-trimethylbicyclo[2.2.1]heptan-2-yl (E)-3-(3,4-dibenzyloxy-5-methoxyphenyl)acrylate (11.8 g).

(1R,2S,4R)-1,7,7-trimethylbicyclo[2.2.1]heptan-2-yl (E)-3-(3,4-dibenzyloxy-5-methoxy phenyl)acrylate (11.1 g, 0.021 mol) was added into tetrahydrofuran (90 ml). The mixture was stirred well, and ammonium formate (13.7 g, 0.21 mol) and palladium carbon (3.6 g, 0.29 mol) were added in sequence. The mixture was reacted for 3 h. After the reaction was completed, palladium carbon was filtered with Celite, and washed with an appropriate amount of tetrahydrofuran. The filtrate was evaporated to dryness. The residue was recrystallized from petroleum ether or isopropanol to obtain 5.8 g of (1R,2S,4R)-1,7,7-trimethylbicyclo [2.2.1]heptan-2-yl (E)-3-(3,4-hydroxy-5-methoxyphenyl) acrylate as a white powder solid with a yield of 79.4%.

(2) At room temperature, (1R,2S,4R)-1,7,7-trimethylbicyclo[2.2.1]heptan-2-yl (E)-3-(3,4-hydroxy-5-methoxyphenyl)acrylate (1.0 g, 2.9 mmol) was added to methanol (20 ml), 10% palladium carbon (0.1 g) was added, and then ammonium formate (2.7 g, 43.5 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.93 g of white powder with a yield of 92.5%. EI-MS M/Z 349.2[M$^+$], 347.2[M$^-$].

Example 13 Synthesis of a Compound of Formula C (1) (E)-4-benzyloxy-3,5-dimethoxyphenylacrylic acid (8.2 g, 0.026 mol) was added into dichloromethane (50 ml). The mixture was cooled in an ice-salt bath to 0° C., and dicyclohexylcarbodiimide (5.43 g, 0.026 mol) and 4-dimethylaminopyridine (0.96 g, 0.008 mol) were added. A drying tube was equipped and the mixture was reacted for 1 h. (1R,2S,4R)-1,7,7-trimethylbicyclo[2.2.1]heptan-2-ol (4.1 g, 0.026 mol) was dissolved in dichloromethane (25 ml) and added dropwise to the reaction solution. After dropwise addition, the ice-salt bath was removed, and the reaction was naturally warmed for overnight. After the reaction was completed, solids were filtered, and the filter cake was washed with an appropriate amount of dichloromethane. The filtrate was evaporated to dryness, and the residue was subjected to column chromatography to obtain (1R,2S,4R)-1,7,7-trimethylbicyclo[2.2.1]heptan-2-yl (E)-3-(4-benzyloxy-3,5-dimethoxyphenyl)acrylate (10.3 g).

(1R,2S,4R)-1,7,7-trimethylbicyclo[2.2.1]heptan-2-yl (E)-3-(4-benzyloxy-3,5-dimethoxy phenyl)acrylate (9.5 g, 0.021 mol) was added into tetrahydrofuran (90 ml). The mixture was stirred well, and ammonium formate (6.8 g, 0.105 mol) and palladium carbon (1.8 g, 0.147 mol) were added in sequence. The mixture was reacted for 3 h. After the reaction was completed, palladium carbon was filtered with Celite, and washed with an appropriate amount of tetrahydrofuran. The filtrate was evaporated to dryness. The residue was recrystallized from petroleum ether or isopropanol to obtain 6.2 g of white powder with a yield of 81.6%.

(2) At room temperature, (1R,2S,4R)-1,7,7-trimethylbicyclo[2.2.1]heptan-2-yl (E)-3-(4-hydroxy-3,5-dimethoxyphenyl)acrylate (1.0 g, 2.8 mmol) was added to methanol (20 ml), 10% palladium carbon (0.1 g) was added, and then ammonium formate (3.2 g, 42 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.91 g of white powder with a yield of 90.5%. EI-MS M/Z 363.5[M$^+$], 361.7[M$^-$].

Example 14 Synthesis of a Compound of Formula D (1) (E)-2-bromo-4-benzyloxy-5-methoxyphenylacrylic acid (9.4 g, 0.026 mol) was added into dichloromethane (50 ml). The mixture was cooled in an ice-salt bath to 0° C., and dicyclohexylcarbodiimide (5.43 g, 0.026 mol) and 4-dimethylaminopyridine (0.96 g, 0.008 mol) were added. A drying tube was equipped and the mixture was reacted for 1 h. (1R,2S,4R)-1,7,7-trimethylbicyclo[2.2.1]heptan-2-ol (4.1 g, 0.026 mol) was dissolved in dichloromethane (25 ml) and added dropwise to the reaction solution. After dropwise addition, the ice-salt bath was removed, and the reaction was naturally warmed for overnight. After the reaction was completed, solids were filtered, and the filter cake was washed with an appropriate amount of dichloromethane. The filtrate was evaporated to dryness, and the residue was subjected to column chromatography to obtain (1R,2S,4R)-1,7,7-trimethylbicyclo[2.2.1]heptan-2-yl (E)-3-(4-benzyloxy-2-bromo-5-methoxyphenyl)acrylate (11.1 g).

(1R,2S,4R)-1,7,7-trimethylbicyclo[2.2.1]heptan-2-yl (E)-3-(4-benzyloxy-2-bromo-5-methoxy phenyl)acrylate (10.5 g, 0.021 mol) was added into tetrahydrofuran (90 ml). The mixture was stirred well, and ammonium formate (6.8 g, 0.105 mol) and palladium carbon (1.8 g, 0.147 mol) were added in sequence. The mixture was reacted for 3 h. After the reaction was completed, palladium carbon was filtered with Celite, and washed with an appropriate amount of tetrahydrofuran. The filtrate was evaporated to dryness. The residue was recrystallized from petroleum ether or isopropanol to obtain 7.3 g of white powder with a yield of 84.9%.

(2) At room temperature, (1R,2S,4R)-1,7,7-trimethylbicyclo[2.2.1]heptan-2-yl (E)-3-(2-bromo-4-hydroxy-5-methoxyphenyl)acrylate (1.0 g, 2.4 mmol) was added to methanol (20 ml), 10% palladium carbon (0.1 g) was added, and then ammonium formate (2.7 g, 43.2 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.94 g of white powder with a yield of 93.5%. EI-MS M/Z 411.1[M$^+$], 409.3[M$^-$].

Example 15 Synthesis of a Compound of Formula E (1) (E)-4-benzyloxy-3-trifluoromethoxyphenylacrylic acid (8.8 g, 0.026 mol) was added into dichloromethane (50 ml). The mixture was cooled in an ice-salt bath to 0° C., and dicyclohexylcarbodiimide (5.43 g, 0.026 mol) and 4-dimethylaminopyridine (0.96 g, 0.008 mol) were added. A drying tube was equipped and the mixture was reacted for 1 h. (1R,2S,4R)-1,7,7-trimethylbicyclo[2.2.1]heptan-2-ol (4.1 g, 0.026 mol) was dissolved in dichloromethane (25 ml) and added dropwise to the reaction solution. After dropwise addition, the ice-salt bath was removed, and the reaction was naturally warmed for overnight. After the reaction was completed, solids were filtered, and the filter cake was washed with an appropriate amount of dichloromethane. The filtrate was evaporated to dryness, and the residue was subjected to column chromatography to obtain (1R,2S,4R)-1,7,7-trimethylbicyclo[2.2.1]heptan-2-yl (E)-3-(4-benzyloxy-3-trifluoromethoxyphenyl)acrylate (9.8 g).

(1R,2S,4R)-1,7,7-trimethylbicyclo[2.2.1]heptan-2-yl (E)-3-(4-benzyloxy-3-trifluoromethoxy phenyl)acrylate (10.0 g, 0.021 mol) was added into tetrahydrofuran (90 ml). The mixture was stirred well, and ammonium formate (6.8 g, 0.105 mol) and palladium carbon (1.8 g, 0.147 mol) were added in sequence. The mixture was reacted for 3 h. After the reaction was completed, palladium carbon was filtered with Celite, and washed with an appropriate amount of tetrahydrofuran. The filtrate was evaporated to dryness. The residue was recrystallized from petroleum ether or isopropanol to obtain 6.5 g of white powder with a yield of 80.2%.

(2) At room temperature, (1R,2S,4R)-1,7,7-trimethylbicyclo[2.2.1]heptan-2-yl (E)-3-(4-hydroxy-3-trifluoromethoxyphenyl)acrylate (1.0 g, 2.6 mmol) was added to methanol (20 ml), 10% palladium carbon (0.1 g) was added, and then ammonium formate (3.6 g, 57.1 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.96 g of white powder with a yield of 95.5%. EI-MS M/Z 387.2[M$^+$], 385.3[M$^-$].

Example 16 Synthesis of a Compound of Formula A (1) (1R,2S,4R)-1,7,7-trimethylbicyclo[2.2.1]heptan-2-ol (18.5 g, 0.12 mol) and 4-dimethylaminopyridine (17.6 g, 0.144 mol) were dissolved in dichloromethane (185 ml). The mixture was cooled to 0° C. with an ice bath, and a solution of chloroacetyl chloride (16.2 g, 0.132 mol) in dichloromethane (160 ml) was slowly added dropwise within 1 h. After dropwise addition, the mixture was continued reacting at 0° C. for 3 h. After the reaction was completed, the reaction solution was poured into ice water (250 g) and stirred for 0.5 h. Liquid layers were separated. The aqueous layer was removed, and the organic layer was washed with a 1N hydrochloric acid solution (70 ml), water (70 ml), and saturated brine (70 ml), dried with anhydrous sodium sulfate for 4 h, and filtered. The filtrate was concentrated to dryness to obtain (1R,2S,4R)-1,7,7-trimethylbicyclo[2.2.1]heptan-2-yl-chloroacetate (25.3 g).

(1R,2S,4R)-1,7,7-trimethylbicyclo[2.2.1]heptan-2-yl-chloroacetate (21.5 g, 0.093 mol), triphenylphosphine (48.9 g, 0.186 mol), and toluene (215 ml) were added into a reaction flask. The mixture was heated to reflux, and reacted for 12 h. The reaction was evaporated to dryness under reduced pressure. The residue was recrystallized from dichloromethane/petroleum ether to obtain (2-oxo-2-(((1R,2S,4R)-1,7,7-trimethylbicyclo[2.2.1]heptan-2-yl)oxy)ethyl-triphenylphosphine hydrochloride (34.2 g).

Under nitrogen protection, (2-oxo-2-(((1R,2S,4R)-1,7,7-trimethylbicyclo[2.2.1]heptan-2-yl)oxy)ethyltriphenylphosphine hydrochloride (34.2 g, 0.069 mol) was added to anhydrous tetrahydrofuran (342 ml). The mixture was cooled to −78° C., and n-butyl lithium (11.0 g, 0.173 mol) was added dropwise. After dropwise addition, the mixture was reacted for 0.5 h. A solution of 3-fluoro-4-hydroxy-5-methoxybenzaldehyde (12.9 g, 0.076 mol) in tetrahydrofuran (70 ml) was added dropwise. After dropwise addition, the reaction was kept at −78° C. for 3 h. After the reaction was completed, the solution was naturally warmed to room temperature. A saturated NaHCO$_3$ solution (200 ml) was added dropwise to the reaction solution. The mixture was then extracted with ethyl acetate (150 ml×3). Organic phases were combined, washed with saturated brine, dried with anhydrous sodium sulfate for 4 h, and filtered. The filtrate was concentrated to dryness. The residue was recrystallized from petroleum ether or isopropanol to obtain 15.2 g of (1R,2S,4R)-1,7,7-trimethylbicyclo[2.2.1]heptan-2-yl (E)-3-(3-fluoro-4-hydroxy-5-methoxyphenyl)acrylate as a white powder solid with a yield of 63.3%.

(2) At room temperature, (1R,2S,4R)-1,7,7-trimethylbicyclo[2.2.1]heptan-2-yl (E)-3-(3-fluoro-4-hydroxy-5-methoxyphenyl)acrylate (1.0 g, 2.9 mmol) was added to methanol (20 ml), 10% palladium carbon (0.1 g) was added, and then ammonium formate (3.6 g, 57.1 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.92 g of white powder with a yield of 91.4%. EI-MS M/Z 351.1[M⁺], 349.3 [M⁻].

Example 17 Synthesis of a Compound of Formula B (1) Under nitrogen protection, (2-oxo-2-(((1R,2S,4R)-1,7,7-trimethylbicyclo[2.2.1]heptan-2-yl)oxy)ethyltriphenylphosphine hydrochloride (34.2 g, 0.069 mol) was added to anhydrous tetrahydrofuran (342 ml). The mixture was cooled to −78° C., and n-butyl lithium (15.4 g, 0.242 mol) was added dropwise. After dropwise addition, the mixture was reacted for 0.5 h. A solution of 3,4-dihydroxy-5-methoxybenzaldehyde (12.8 g, 0.076 mol) in tetrahydrofuran (70 ml) was added dropwise. After dropwise addition, the reaction was kept at −78° C. for 3 h. After the reaction was completed, the solution was naturally warmed to room temperature. A saturated NaHCO₃ solution (200 ml) was added dropwise to the reaction solution. The mixture was then extracted with ethyl acetate (150 ml×3). Organic phases were combined, washed with saturated brine, dried with anhydrous sodium sulfate for 4 h, and filtered. The filtrate was concentrated to dryness. The residue was recrystallized from petroleum ether or isopropanol to obtain 14.8 g of (1R,2S,4R)-1,7,7-trimethylbicyclo[2.2.1]heptan-2-yl (E)-3-(3,4-hydroxy-5-methoxy phenyl)acrylate as a white powder solid with a yield of 61.9%.

(2) At room temperature, (1R,2S,4R)-1,7,7-trimethylbicyclo[2.2.1]heptan-2-yl (E)-3-(3,4-hydroxy-5-methoxyphenyl)acrylate (1.0 g, 2.9 mmol) was added to methanol (20 ml), 10% palladium carbon (0.1 g) was added, and then ammonium formate (3.6 g, 57.1 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.93 g of white powder with a yield of 92.5%. EI-MS M/Z 349.2[M⁺], 347.2[M⁻].

Example 18 Synthesis of a Compound of Formula C (1) Under nitrogen protection, (2-oxo-2-(((1R,2S,4R)-1,7,7-trimethylbicyclo[2.2.1]heptan-2-yl)oxy)ethyltriphenylphosphine hydrochloride (34.2 g, 0.069 mol) was added to anhydrous tetrahydrofuran (342 ml). The mixture was cooled to −78° C., and n-butyl lithium (11.0 g, 0.173 mol) was added dropwise. After dropwise addition, the mixture was reacted for 0.5 h. A solution of 4-hydroxy-3,5-dimethoxybenzaldehyde (13.8 g, 0.076 mol) in tetrahydrofuran (70 ml) was added dropwise. After dropwise addition, the reaction was kept at −78° C. for 3 h. After the reaction was completed, the solution was naturally warmed to room temperature. A saturated NaHCO₃ solution (200 ml) was added dropwise to the reaction solution. The mixture was then extracted with ethyl acetate (150 ml×3). Organic phases were combined, washed with saturated brine, dried with anhydrous sodium sulfate for 4 h, and filtered. The filtrate was concentrated to dryness. The residue was recrystallized from petroleum ether or isopropanol to obtain 16.2 g of (1R,2S,4R)-1,7,7-trimethylbicyclo[2.2.1]heptan-2-yl (E)-3-(4-hydroxy-3,5-dimethoxy phenyl)acrylate as a white powder solid with a yield of 65.1%.

(2) At room temperature, (1R,2S,4R)-1,7,7-trimethylbicyclo[2.2.1]heptan-2-yl (E)-3-(4-hydroxy-3,5-dimethoxyphenyl)acrylate (1.0 g, 2.8 mmol) was added to methanol (20 ml), 10% palladium carbon (0.1 g) was added, and then ammonium formate (3.6 g, 57.1 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.95 g of white powder with a yield of 94.5%. EI-MS M/Z 363.5[M⁺], 361.7[M⁻].

Example 19 Synthesis of a Compound of Formula D (1) Under nitrogen protection, (2-oxo-2-(((1R,2S,4R)-1,7,7-trimethylbicyclo[2.2.1]heptan-2-yl)oxy)ethyltriphenylphosphine hydrochloride (34.2 g, 0.069 mol) was added to anhydrous tetrahydrofuran (342 ml). The mixture was cooled to −78° C., and n-butyl lithium (11.0 g, 0.173 mol) was added dropwise. After dropwise addition, the mixture was reacted for 0.5 h. A solution of 2-bromo-4-hydroxy-5-methoxybenzaldehyde (17.6 g, 0.076 mol) in tetrahydrofuran (70 ml) was added dropwise. After dropwise addition, the reaction was kept at −78° C. for 3 h. After the reaction was completed, the solution was naturally warmed to room temperature. A saturated NaHCO₃ solution (200 ml) was added dropwise to the reaction solution. The mixture was then extracted with ethyl acetate (150 ml×3). Organic phases were combined, washed with saturated brine, dried with anhydrous sodium sulfate for 4 h, and filtered. The filtrate was concentrated to dryness. The residue was recrystallized from petroleum ether or isopropanol to obtain 17.6 g of (1R,2S,4R)-1,7,7-trimethylbicyclo[2.2.1]heptan-2-yl (E)-3-(2-bromo-4-hydroxy-5-methoxy phenyl)acrylate as a white powder solid with a yield of 62.4%.

(2) At room temperature, (1R,2S,4R)-1,7,7-trimethylbicyclo[2.2.1]heptan-2-yl (E)-3-(2-bromo-4-hydroxy-5-methoxyphenyl)acrylate (1.0 g, 2.4 mmol) was added to methanol (20 ml), 10% palladium carbon (0.1 g) was added, and then ammonium formate (3.6 g, 57.1 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.93 g of white powder with a yield of 92.5%. EI-MS M/Z 411.1[M⁺], 409.3[M⁻].

Example 20 Synthesis of a Compound of Formula E (1) Under nitrogen protection, (2-oxo-2-(((1R,2S,4R)-1,7,7-trimethylbicyclo[2.2.1]heptan-2-yl)oxy)ethyltriphenylphosphine hydrochloride (34.2 g, 0.069 mol) was added to anhydrous tetrahydrofuran (342 ml). The mixture was cooled to −78° C., and n-butyl lithium (11.0 g, 0.173 mol) was added dropwise. After dropwise addition, the mixture was reacted for 0.5 h. A solution of 3-trifluoromethoxy-4-hydroxybenzaldehyde (15.7 g, 0.076 mol) in tetrahydrofuran (70 ml) was added dropwise. After dropwise addition, the temperature was kept at −78° C. for 3 h. After the reaction was completed, the solution was naturally warmed to room temperature. A saturated NaHCO₃ solution (200 ml) was added dropwise to the reaction solution. The mixture was then extracted with ethyl acetate (150 ml×3). Organic phases were combined, washed with saturated brine, dried with anhydrous sodium sulfate for 4 h, and filtered. The filtrate was concentrated to dryness. The residue was recrystallized from petroleum ether or isopropanol to obtain 16.3 g of (1R,2S,4R)-1,7,7-trimethylbicyclo[2.2.1]heptan-2-yl (E)-3-(4-hydroxy-3-trifluoromethoxyphenyl) acrylate as a white powder solid with a yield of 61.5%.

(2) At room temperature, (1R,2S,4R)-1,7,7-trimethylbicyclo[2.2.1]heptan-2-yl (E)-3-(4-hydroxy-3-trifluoromethoxyphenyl)acrylate (1.0 g, 2.6 mmol) was added to methanol (20 ml), 10% palladium carbon (0.1 g) was added, and then ammonium formate (3.6 g, 57.1 mmol) was added. The mixture was stirred at room temperature for 3 h. After the reaction was completed, the solution was filtered, and the filtrate was concentrated to dryness. The residue was extracted with 20 ml of ethyl acetate and 20 ml of water. The layer of ethyl acetate was dried with anhydrous sodium sulfate for 4 h and filtered, and the filtrate was concentrated to dryness to obtain 0.96 g of white powder with a yield of 95.5%. EI-MS M/Z 387.2[M$^+$], 385.3[M$^-$].

Example 21

In this example, phenylpropionate compounds were studied for pharmacodynamic mechanism, with aspirin (administrated at 4.0 mg/kg), D-bornyl ferulate (administrated at 4.0 mg/kg), and D-tanshinol borneol ester (administrated at 4.0 mg/kg) as positive control drugs. Structures of aspirin, D-bornyl ferulate (Patent Application No.: 201510243181.5), and D-tanshinol borneol ester compounds are as follows:

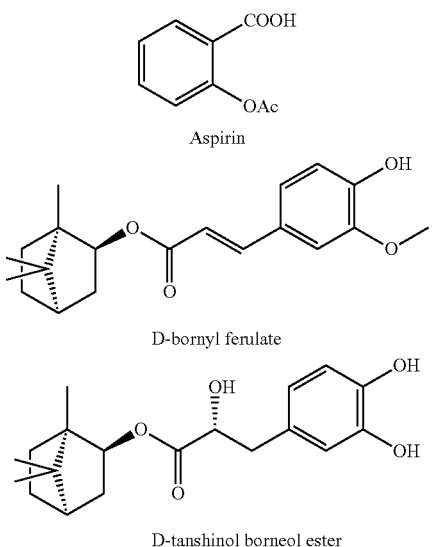

D-Tanshinol Borneol Ester

Trial method: Effects on inflammatory factors and blood viscosity of rats with acute cerebral ischemia-reperfusion: 70 Male SD rats underwent an MACO surgery by a suture method, and after the surgery, alive rats were randomly grouped (into 7 groups, the number of successful animals in each group was guaranteed to be 6 to 8). Blood perfusion was recovered 2 h after MCAO, and corresponding trial medicaments were intravenously injected 2 h after blood reperfusion. 4 hours after the administration, blood was collected and the rats were sacrificed to take out brain tissues. The brain tissues and part of the blood were centrifuged to collect serum which was detected for inflammatory factors, and part of the blood was detected for blood viscosity by using a blood viscometer. Detected indicators: cerebral infarction area; inflammatory factors IL-1β and TNF-α; and blood viscosity.

Table 1 lists results of effects of phenylpropionate compounds (4 mg/kg) on cerebral infarction area of rats with acute cerebral ischemia (n=5).

TABLE 1

| Group | Cerebral Infarction Area | Percentage of Cerebral Infarction Area Reduction (%) |
| --- | --- | --- |
| Solvent control | 36.7 ± 1.33 | |
| Aspirin | 22.7 ± 4.05*** | 38.0 |
| D-bornyl ferulate | 21.7 ± 4.35*** | 40.9 |
| D-tanshinol borneol ester | 25.6 ± 4.65*** | 30.2 |
| Compound A | 18.6 ± 2.65*** | 49.3 |
| Compound B | 18.7 ± 7.16*** | 49.0 |
| Compound C | 19.6 ± 5.38*** | 46.6 |
| Compound D | 19.4 ± 4.61*** | 47.1 |
| Compound E | 19.8 ± 3.61*** | 46.0 |

*P < 0.001, P < 0.01, *P < 0.05 compared with the solvent control group

As can be seen from the results in Table 1, some phenylpropionate compounds exhibit better trial results on a SD rat model of focal ischemia-reperfusion than the positive control drugs D-bornyl ferulate and D-tanshinol borneol ester, and have good pharmacodynamic effect of reducing cerebral infarction area.

Table 2 lists results of effects of phenylpropionate compounds (4 mg/kg) on blood viscosity of rats (n=5).

TABLE 2

| Group | High Shear | Low Shear |
| --- | --- | --- |
| Solvent control | 3.07 ± 0.194 | 15.8 ± 0.422 |
| Aspirin | 2.64 ± 0.199*** | 12.2 ± 0.742*** |
| D-bornyl ferulate | 2.84 ± 0.323* | 13.8 ± 0.574** |
| D-tanshinol borneol ester | 2.76 ± 0.134** | 14.1 ± 0.658** |
| Compound A | 2.56 ± 0.057*** | 13.2 ± 0.535*** |
| Compound B | 2.73 ± 0.122** | 13.9 ± 0.134** |
| Compound C | 2.70 ± 0.982** | 13.9 ± 1.014** |
| Compound D | 2.63 ± 0.312*** | 13.3 ± 0.354*** |
| Compound E | 2.73 ± 0.405** | 13.5 ± 1.183*** |

*P < 0.001, P < 0.01, *P < 0.05 compared with the solvent control group

As can be seen from the results in Table 2, some phenylpropionate compounds exhibit comparable effects in reducing blood viscosity in rats to positive control drugs aspirin, D-bornyl ferulate, and D-tanshinol borneol ester, which indicates that these phenylpropionate compounds might have the effects of increasing cerebral blood flow and improving cerebral hemorheology in stroke patients.

Table 3 lists results of effects of phenylpropionate compounds (4 mg/kg) on inflammatory factors in blood and brain tissues of rats (n=5).

TABLE 3

| Group | TNF-α (ng/L) | IL-1β (ng/L) |
| --- | --- | --- |
| Solvent control | 758 ± 9.36 | 84.5 ± 8.50 |
| Aspirin | 647 ± 45.2** | 62.9 ± 11.5** |
| D-bornyl ferulate | 658 ± 23.6** | 64.8 ± 5.8** |

TABLE 3-continued

| Group | TNF-α (ng/L) | IL-1β (ng/L) |
|---|---|---|
| D-tanshinol borneol ester | 687 ± 35.4* | 67.1 ± 8.8** |
| Compound A | 615 ± 42.9** | 53.8 ± 6.4*** |
| Compound B | 645 ± 42.3** | 63.4 ± 5.6** |
| Compound C | 634 ± 25.1** | 59.3 ± 8.7** |
| Compound D | 562 ± 34.2*** | 53.4 ± 8.9*** |
| Compound E | 573 ± 43.0*** | 64.3 ± 8.1** |

*P < 0.001, P < 0.01, *P < 0.05 compared with the solvent control group

As can be seen from the results in Table 3, some phenylpropionate compounds exhibit comparable or even better anti-inflammatory effects than positive control drugs aspirin, D-bornyl ferulate, and D-tanshinol borneol ester, which indicates that these phenylpropionate compounds have the effect of ameliorating inflammatory responses in stroke patients.

Effects on maximum platelet aggregation rate of rabbits: 3 Rabbits were anesthetized, and blood was collected from the heart to obtain 14 parts of plasma for each rabbit (1 ml per part of plasma). 7 Parts were induced with ADP to allow platelet aggregation, and 7 parts were induced with a platelet activating factor. After the induction, a solvent, positive control drug aspirin, and 5 samples to be trialed were separately added to the plasma, and maximum platelet aggregation rate was detected with a platelet aggregation meter. The trials were repeated 3 times, and an average was taken. Detected indicator: maximum platelet aggregation rate.

Table 4 lists results of effects of phenylpropionate compounds (4 mg/kg) on platelet aggregation rate of rabbits (n=3).

TABLE 4

| | Induced with ADP | | | Induced with PAF | |
|---|---|---|---|---|---|
| Group | Maximum Aggregation Rate (%) | Inhibition rate on Aggregation (%) | Group | Maximum Aggregation Rate (%) | Inhibiton rate on Aggregation (%) |
| Blank control | 32.9 ± 0.92 | | Blank control | 71.4 ± 5.06 | |
| Solvent control | 32.2 ± 1.37 | | Solvent control | 69.8 ± 1.55 | |
| Aspirin | 14.8 ± 3.99*** | 54.1 | Aspirin | 41.3 ± 1.53*** | 40.8 |
| D-bornyl ferulate | 17.6 ± 4.59*** | 46.5 | D-bornyl ferulate | 45.4 ± 2.64*** | 36.4 |
| D-tanshinol borneol ester | 18.5 ± 4.36** | 43.8 | D-tanshinol borneol ester | 47.3 ± 4.53*** | 33.8 |
| Compound A | 15.7 ± 6.31*** | 52.3 | Compound A | 28.4 ± 6.4*** | 60.2 |
| Compound B | 17.5 ± 2.84*** | 46.8 | Compound B | 32.1 ± 9.7*** | 55.0 |
| Compound C | 14.3 ± 5.64*** | 56.5 | Compound C | 33.6 ± 7.9*** | 52.9 |
| Compound D | 14.7 ± 7.42*** | 55.3 | Compound D | 46.7 ± 9.8*** | 34.6 |
| Compound E | 17.7 ± 5.46*** | 46.2 | Compound E | 43.5 ± 8.4*** | 39.1 |

*P < 0.001, P < 0.01, *P < 0.05 compared with the solvent control group

As can be seen from the results in Table 4, some phenylpropionate compounds exhibit comparable effects in inhibiting platelet aggregation as positive control drugs aspirin, D-bornyl ferulate, and D-tanshinol borneol ester, which indicates that these phenylpropionate compounds might have the effect of inhibiting the continuous generation of embolisms in stroke patients.

The above-mentioned trial results indicate that the phenylpropionate compounds have good anti-stroke effects.

Example 22

In this example, phenylpropionate compounds were studied for dose-effect relationship, with D-bornyl ferulate (administrated at 4.0 mg/kg) and D-tanshinol borneol ester (administrated at 4.0 mg/kg) as positive control drugs. Structures of D-bornyl ferulate (Patent Application No.: 201510243181.5) and D-tanshinol borneol ester compounds are as follows:

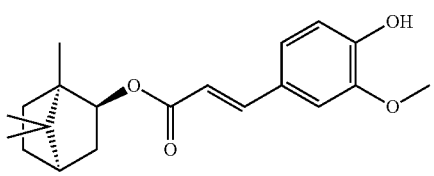

D-bornyl ferulate

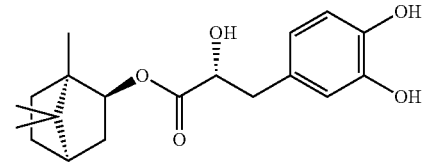

D-tanshinol borneol ester

Trial method: A cerebral ischemia reperfusion model of middle cerebral artery occlusion (MCAO) was prepared by an internal carotid artery suture method. An animal was anesthetized with 10% chloral hydrate (3.6 mL/kg) and then fixed on an operating table in a supine position. Its skin was disinfected, and a midline incision was made on the neck. The right common carotid artery, external carotid artery, and internal carotid artery were separated, the vagus nerve was gently striped off, and the external carotid artery was ligated and cut. The common carotid artery was clamped at the proximal end. An incision was made on the external carotid artery at the distal end from the ligature, and a nylon thread which had an outer diameter of 0.285 mm and had a polished and lubricated tip was inserted. The nylon thread was advanced through the bifurcation of the common carotid artery into the internal carotid artery, and then was slowly inserted until there was slight resistance (about 20 mm from the bifurcation) to block all the blood supply to the middle cerebral artery. 2 h after cerebral ischemia, the nylon thread was gently pulled out to restore blood supply for reperfusion, and the neck skin was sutured and disinfected. The animal was put back in a cage and raised. During the modeling operation, animals with abnormal conditions due to anesthesia, surgery, etc. were excluded, and successfully modeled animals were randomly grouped. Schemes were set according to different trial doses, and drug treatment was given 2 h after cerebral ischemia-reperfusion. Death conditions were recorded every day after the surgery, and indicators were evaluated after 48 h. In the whole trial process, general conditions were observed, mainly including: death, coma, breathing, urine and feces traits, hair colors, mental status, vomiting and vomitus, bleeding, convulsion, spasm, etc. Abnormal animals due to unexpected factors were excluded. Finally, unblinding was conducted by a person who made blind trials.

Evaluated indicator: (1) Evaluation of symptoms of neurological deficits: The symptoms of neurological deficits were evaluated by using a modified Bederson 5-point scale. A single-blind method was used for evaluating the symptoms of neurological deficits in rats with brain trauma. That is, a trial designer marked animals in accordance with groups, and an experimenter who scored the symptoms of neurological deficits had no knowledge of how the animals were grouped. After scoring was completed, the scorer submitted scoring results for various marks to the designer, and the designer performed unblinding to obtain scores of animals in each trial group. Scoring criteria are listed in Table 5. (2) Measurement of cerebral infarction area: A method reported in the literature was used. An animal was anesthetized with 10% chloral hydrate and decapitated to collect brain. The olfactory bulb, cerebellum and lower brain stem were removed. Blood stains on the surface of the brain were rinsed with normal saline, the residual water stains on the surface were absorbed, and the brain was placed at −80° C. for 7 min. After the brain was taken out, a coronal section was immediately made at downwards and vertical to the sight intersection plane, and brain slices were made every 2 mm backwards. Brain slices were placed in a TTC (20 g/L) dye solution prepared with 0.9% normal saline, and incubated at 37° C. for 90 min. Normal brain tissues were stained deep red, and ischemic brain tissues were pale-white. After rinsed with normal saline, the brain sections were quickly arranged in order from front to back, the residual water stains on the surface were absorbed to dryness, and pictures were taken. Image analysis software was used for statistics on the pictures. Ischemic area (white region) on the right side and total area on the right side were delineated, and a percentage of the cerebral infarction area was calculated by the following formula:

$$\text{Cerebral infarction area \%} = 100 \times \frac{\text{total ischemic area}}{\text{total area on the right side}}.$$

TABLE 5

| Score | Symptoms of Neurological Deficits |
|---|---|
| 0 | When held by the tail and suspended in the air, the animal extends both forelimbs toward the floor and has no other behavioral deficits. |
| 1 | When held by the tail and suspended in the air, the forelimb contralateral (left) to the operated side of the animal exhibit wrist and elbow flexion, shoulder internal rotation, and elbow abduction, and is tightly against the chest wall. |
| 2 | When the animal is placed on a smooth plate and is pushed the operated shoulder to allow move towards the contralateral side, there is a reduced resistance. |

TABLE 5-continued

| Score | Symptoms of Neurological Deficits |
|---|---|
| 3 | When allowed to walk freely, the animal circles contralateral towards the operated side. |
| 4 | Limbs are paralyzed and cannot move spontaneously. |

Statistical analysis: Quantitative data is expressed as mean value±standard error. One-way analysis of variance was used for cerebral infarction area and scoring of the symptoms of neurological deficits. Significant difference between two groups was measured by a Scheffe's test. The mortality rate was tested by ANOVA. A difference of P<0.05 was defined as significant.

Figure 2:
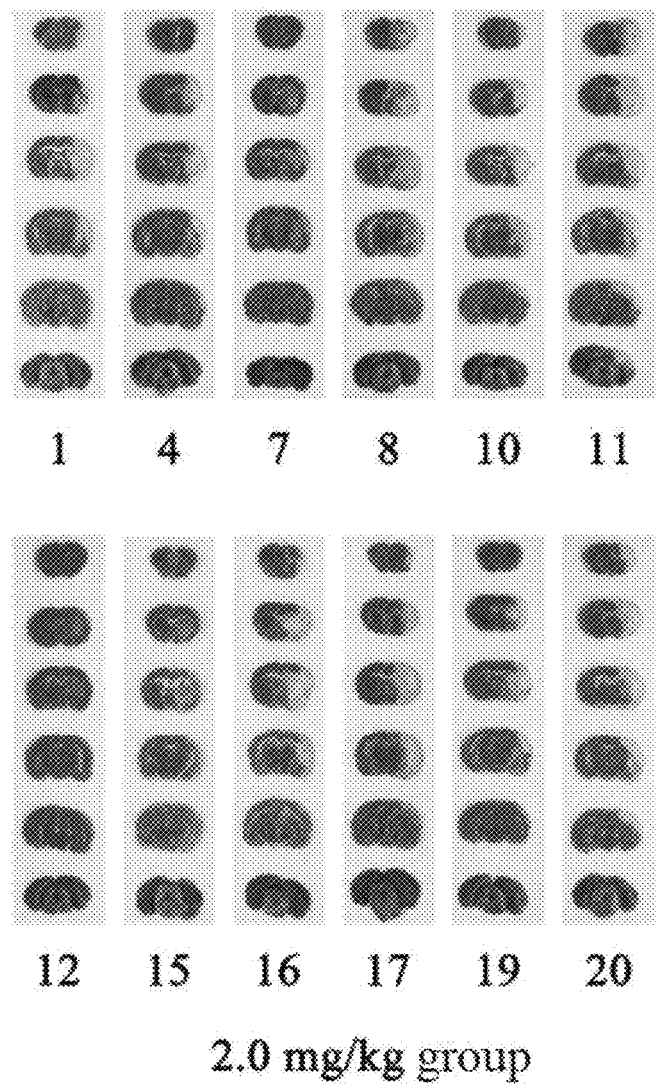
FIG. 2 is a diagram of brain slices in pharmacodynamic trials of Compound A administered at 2.0 mg/kg.
Figure 3:
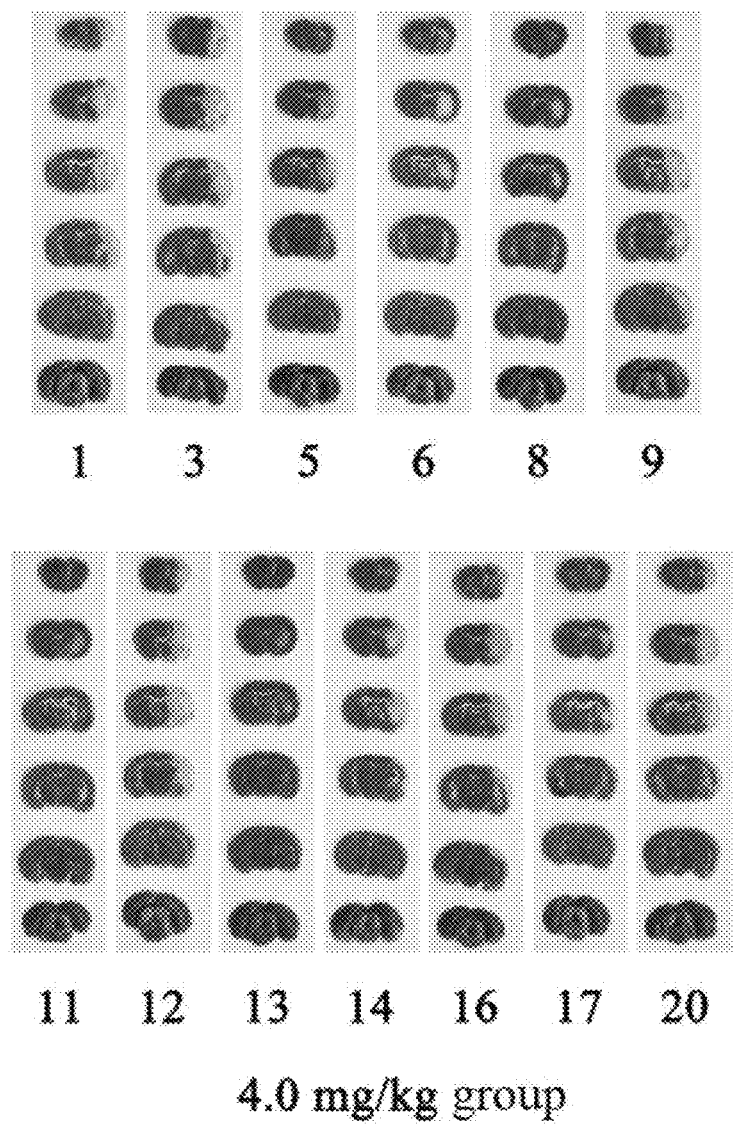
FIG. 3 is a diagram of brain slices in pharmacodynamic trials of Compound A administered at 4.0 mg/kg.
Figure 4:
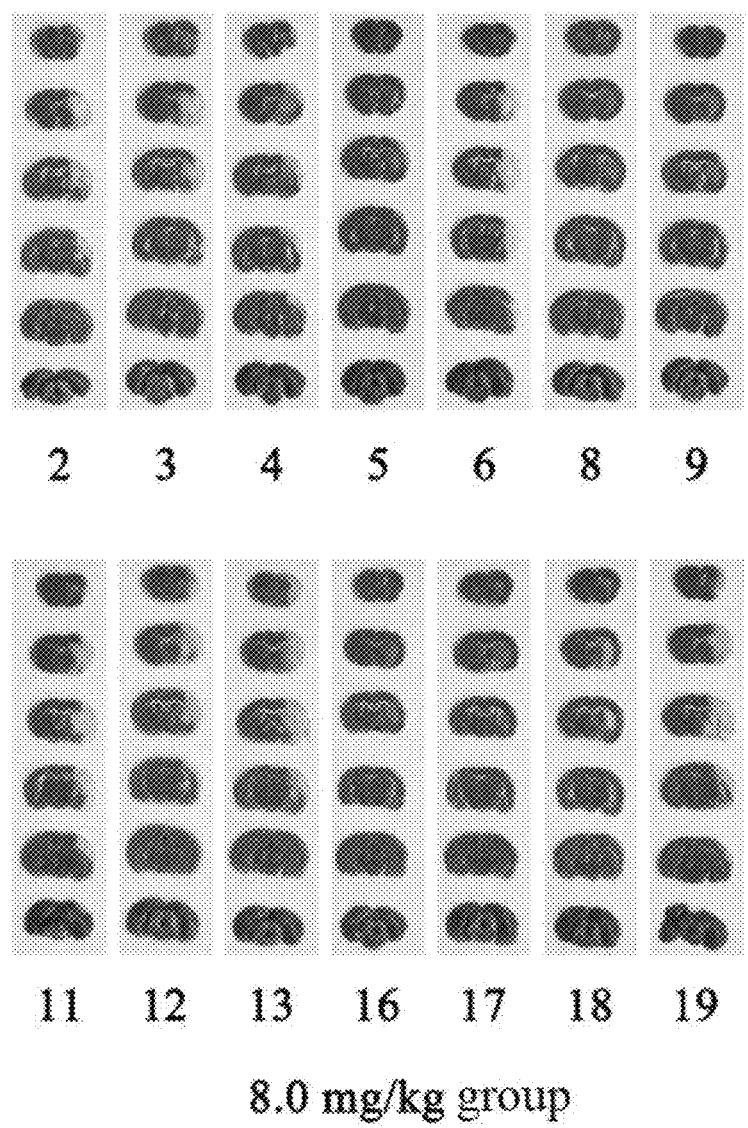
FIG. 4 is a diagram of brain slices in pharmacodynamic trials of Compound A administered at 8.0 mg/kg.

The effect of Compound A on a SD rat model of focal ischemia-reperfusion is shown in Table 6. As can be seen from results in Table 6, compared with the model group, the 2.0 mg/kg group, 4.0 mg/kg group, 8.0 mg/kg group, D-bornyl ferulate group, and D-tanshinol borneol ester group have the effect of significantly alleviating infarction area and symptoms of neurological deficits. When administered at 4.0 mg/kg, Compound A is slightly superior to the D-bornyl ferulate group and the D-tanshinol borneol ester group. Brain sections of trial rats are shown in FIGS. 2 to 4.

TABLE 6

| Group | Sample (number) | Infarction area (%) | Score of Symptoms of Neurological Deficits |
|---|---|---|---|
| Sham-operated group | 8 | 0.00 ± 0.00 | 0.00 ± 0.00 |
| Model group | 16 | 37.52 ± 2.17 | 2.94 ± 0.14 |
| D-bornyl ferulate group (4.0 mg/kg) | 16 | 21.68 ± 2.80* | 1.94 ± 0.19* |
| D-tanshinol borneol ester group (4.0 mg/kg) | 15 | 22.76 ± 2.42* | 1.98 ± 0.17* |
| 2.0 mg/kg group | 15 | 24.73 ± 2.63* | 2.05 ± 0.20* |
| 4.0 mg/kg group | 16 | 20.25 ± 2.53* | 1.94 ± 0.19* |
| 8.0 mg/kg group | 17 | 18.38 ± 2.74* | 1.75 ± 0.21* |

Mean value ± standard error.
*$P < 0.05$, compared with the model group

The effect of Compound C on a SD rat model of focal ischemia-reperfusion is shown in Table 7. As can be seen from results in Table 7, compared with the model group, the 2.0 mg/kg group, 4.0 mg/kg group, 8.0 mg/kg group, D-bornyl ferulate group, and D-tanshinol borneol ester group have the effect of significantly alleviating infarction area and symptoms of neurological deficits. When administered at 4.0 mg/kg, Compound C is slightly superior to the D-bornyl ferulate group and the D-tanshinol borneol ester group.

TABLE 7

| Group | Sample (number) | Infarction area (%) | Score of Symptoms of Neurological Deficits |
|---|---|---|---|
| Sham-operated group | 8 | 0.00 ± 0.00 | 0.00 ± 0.00 |
| Model group | 15 | 41.84 ± 2.49 | 3.07 ± 0.12 |
| D-bornyl ferulate group (4.0 mg/kg) | 16 | 21.68 ± 2.80* | 1.94 ± 0.19* |
| D-tanshinol borneol ester group (4.0 mg/kg) | 15 | 22.76 ± 2.42* | 1.98 ± 0.17* |
| 2.0 mg/kg group | 15 | 22.24 ± 2.84* | 2.45 ± 0.13* |
| 4.0 mg/kg group | 15 | 21.04 ± 2.14* | 2.18 ± 0.23* |
| 8.0 mg/kg group | 16 | 19.32 ± 3.53* | 1.98 ± 0.14* |

Mean value ± standard error.
*$P < 0.05$, compared with the model group

The above-mentioned results indicate that Compound A and Compound C have a good effect of treating ischemic cerebral stroke.

Example 23

In this example, Compound A and Compound C were studied for acute toxicity by a method described below.

Trial method: 30 SD rats, half male and half female, were used. The average weight was 160-200 g for female rats and 180-220 g for male rats when grouped. An individual weight should be within ±20% of the average weight. Before trial, animals were accommodated environment for at least 5 days, and healthy rats (female rats should be not pregnant) were selected as trial animals. Matter inspected during the accommodation period mainly was: whether the rats were consistent with quality indicators required in the order; inspection of general condition; and whether the weight was within the weight range required by the trial. Unqualified abnormal animals were excluded from the trial. A single dosage was injected through tail veins of rats at low, medium, or high dose. The doses were adjusted to be 5 mg/kg, 10 mg/kg, and 20 mg/kg, respectively according to blank preparation pre-trials. A control group was set in which a same volume of vehicle was intravenously injected.

Observation method: (1) Observation of general condition: Animals were observed for, including but not limited to, appearance signs, administration sites (whether there was bleeding, redness, bruising, induration, purulence, ulceration happens), hair coats, general behaviors, mental status, gland secretion, skin and mucous membrane colors, respiratory status, feces traits, genitalia, death, etc. and other toxicity symptoms. The rats were observed about 0-2 h and 4-6 h after each administration. If a toxicity symptom occurs, the animal may be observed more times. (2) Gross anatomical observation: On the 8th day of the trial, all surviving rats in each group were dissected and observed, and administration sites and abnormal organs and tissues which were identified through gross anatomical observation to be potentially related to trial samples were photographed and recorded. (3) Disposal of dying animals: Status of rats and observation time were recorded, and their weights were measured. (4) Disposal of dead animals: The time of death or when a rat was found dead were recorded. The rat was measured for weight before quickly dissected for gross observation and speculated for cause of death.

Trial result: SD rats exhibited no obvious toxic side effects and no obvious weight and diet decrease trends after a single-dose intravenous injection of Compound A and Compound C. It shows that the tolerance of Compound A and Compound C is 20 mg/kg.

Example 24

In this example, Compound A was measured for a pharmacodynamic time window by a method described below.

Trial method: A cerebral ischemia reperfusion model of middle cerebral artery occlusion (MCAO) was prepared by an internal carotid artery suture method. An animal was anesthetized with 10% chloral hydrate (3.6 mL/kg) and then fixed on an operating table in a supine position. Its skin was disinfected, and a midline incision was made on the neck. The right common carotid artery, external carotid artery, and internal carotid artery were separated, the vagus nerve was gently striped off, and the external carotid artery was ligated and cut. The common carotid artery was clamped at the proximal end. An incision was made on the external carotid artery at the distal end from the ligature, and a nylon thread which had an outer diameter of 0.285 mm and had a polished and lubricated tip was inserted. The nylon thread was advanced through the bifurcation of the common carotid artery into the internal carotid artery, and then was slowly inserted until there was slight resistance (about 20 mm from the bifurcation) to block all the blood supply to the middle cerebral artery. 2 h after cerebral ischemia, the nylon thread was gently pulled out to restore blood supply for reperfusion, and the neck skin was sutured and disinfected. The animal was put back in a cage and raised. During the modeling operation, animals with abnormal conditions due to anesthesia, surgery, etc. were excluded, and successfully modeled animals were randomly grouped. Schemes were set according to trial doses, and drug treatment was given 3 h, 4 h, and 5 h after cerebral ischemia-reperfusion. Death conditions were recorded every day after the surgery, and indicators were evaluated after 48 h. In the whole trial process, general conditions were observed, mainly including: death, coma, breathing, urine and feces traits, hair colors, mental status, vomiting and vomitus, bleeding, convulsion, spasm, etc. Abnormal animals due to unexpected factors were excluded. Finally, unblinding was conducted by a person who made blind trials.

Evaluated indicator: (1) Evaluation of symptoms of neurological deficits: The symptoms of neurological deficits were evaluated by using a modified Bederson 5-point scale. A single-blind method was used for evaluating the symptoms of neurological deficits in rats with brain trauma. That is, a trial designer marked animals in accordance with groups, and an experimenter who scored the symptoms of neurological deficits had no knowledge of how the animals were grouped. After scoring was completed, the scorer submitted scoring results for various marks to the designer, and the designer performed unblinding to obtain scores of animals in each trial group. Scoring criteria are listed in Table 5 in Example 22. (2) Measurement of cerebral infarction area: A method reported in the literature was used. An animal was anesthetized with 10% chloral hydrate and decapitated to collect brain. The olfactory bulb, cerebellum and lower brain stem were removed. Blood stains on the surface of the brain were rinsed with normal saline, the residual water stains on the surface were absorbed, and the brain was placed at −80° C. for 7 min. After the brain was taken out, a coronal section was immediately made at downwards and vertical to the sight intersection plane, and brain slices were made every 2 mm backwards. Brain slices were placed in a TTC (20 g/L) dye solution prepared with 0.9% normal saline, and incubated at 37° C. for 90 min. Normal brain tissues were stained deep red, and ischemic brain tissues were pale-white. After rinsed with normal saline, the brain sections were quickly arranged in order from front to back, the residual water stains on the surface were absorbed to dryness, and pictures were taken. Image analysis software was used for statistics on the pictures. Ischemic area (white region) on the right side and total area on the right side were delineated, and a percentage of the cerebral infarction area was calculated by the following formula:

$$\text{Cerebral infarction area } \% = 100 \times \frac{\text{total ischemic area}}{\text{total area on the right side}}.$$

Statistical analysis: Quantitative data is expressed as mean value±standard error. One-way analysis of variance was used for cerebral infarction area and scoring of the symptoms of neurological deficits. Significant difference between two groups was measured by a Scheffe's test. The mortality rate was tested by ANOVA. A difference of P<0.05 was defined as significant.

Trial Results:

Measurement results of an administration time window of Compound A for a SD rat model of focal ischemia-reperfusion are listed in Table 8. As can be seen from the results in Table 9, Compound A has a certain treatment time window when administered after ischemia-reperfusion. It shows a significant protective effect when administered 3 h and 4 h after reperfusion, and it shows a certain protective effect when administered after 5 h without statistical difference. Therefore, the treatment time window of the trial drug, Compound A, in the model is not less than 6 h after ischemia.

TABLE 8

| Group | Sample (number) | Infarction area (%) | Score of Symptoms of Neurological Deficits |
|---|---|---|---|
| Sham-operated group | 8 | 0.00 ± 0.00 | 0.00 ± 0.00 |
| Model group | 18 | 35.50 ± 2.18 | 2.83 ± 0.12 |
| 3 h group | 18 | 23.56 ± 2.86* | 2.04 ± 0.12* |
| 4 h group | 18 | 24.54 ± 2.53* | 2.13 ± 0.14* |
| 5 h group | 17 | 32.43 ± 2.13 | 2.42 ± 0.17 |

Mean value ± standard error.
*P < 0.05, compared with the model group

Example 25

In this example, Compounds A to E, D-bornyl ferulate, and D-tanshinol borneol ester were measured for distribution in brain. Structures of D-bornyl ferulate (Patent Application No.: 201510243181.5) and D-tanshinol borneol ester compounds are as follows:

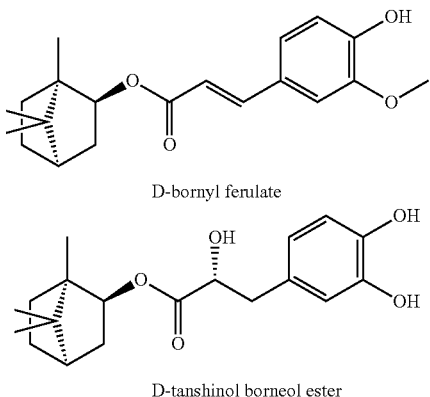

D-bornyl ferulate

D-tanshinol borneol ester

Method for testing distribution in brain: 42 rats with a weight range of 200±20 g were taken. The rats were randomly divided into 7 groups, with 6 rats per group, half male and half female. Rats were fasted with free access to water for 12 h and then intravenously injected with 4 mg/kg of a compound. Rats in the 3 groups were sacrificed through femoral artery bleeding and collected for blood 10 min, 60 min, 180 min after administration, respectively. Brains were taken out, 0.2 g was weighted, and 1 mL of pure water was added for homogenizing. The blood samples and brain homogenate samples were stored at −20° C.

Trial Results:

Distribution of Compounds A to E, and D-bornyl ferulate and D-tanshinol borneol ester compounds in brain: Data on concentrations of Compounds A to E, D-bornyl ferulate, and D-tanshinol borneol ester in plasma and intracerebral in rats intravenously injected with 4 mg/kg of Compounds A to E, D-bornyl ferulate, and D-tanshinol borneol ester are listed in Table 9.

TABLE 9

| Compound | Time (min) | Mean Plasma Concentration (ng/ml) | Mean Intracerebral Concentration (ng/g) | Brain/Blood Concentration Ratio |
|---|---|---|---|---|
| D-bornyl ferulate | 10 | 2893.38 ± 671.02 | 1491.72 ± 218.71 | 0.52 |
| | 60 | 138.28 ± 54.98 | 700.66 ± 136.06 | 5.0 |
| | 180 | 47.13 ± 21.57 | 276.42 ± 81.28 | 5.8 |
| D-tanshinol borneol ester | 10 | 2207.84 ± 546.25 | 1035.64 ± 168.46 | 0.47 |
| | 60 | 243.58 ± 62.35 | 643.86 ± 99.67 | 2.6 |
| | 180 | 52.83 ± 34.13 | 176.58 ± 35.21 | 3.4 |
| Compound A | 10 | 1021.18 ± 192.13 | 2639.21 ± 517.28 | 2.6 |
| | 60 | 251.51 ± 76.45 | 1422.99 ± 308.95 | 5.7 |
| | 180 | 97.32 ± 22.69 | 311.11 ± 115.34 | 3.2 |
| Compound B | 10 | 1534.67 ± 581.23 | 2485.67 ± 436.61 | 1.6 |
| | 60 | 284.56 ± 105.28 | 1267.55 ± 234.26 | 4.5 |
| | 180 | 136.28 ± 60.35 | 246.64 ± 87.53 | 1.8 |
| Compound C | 10 | 906.08 ± 145.12 | 2632.38 ± 167.13 | 2.9 |
| | 60 | 160.39 ± 49.13 | 1870.38 ± 405.62 | 11 |
| | 180 | 92.24 ± 35.46 | 188.48 ± 51.94 | 2.0 |
| Compound D | 10 | 1398.5 ± 235.64 | 2260.54 ± 323.25 | 1.6 |
| | 60 | 312.44 ± 115.35 | 1429.87 ± 284.65 | 4.6 |
| | 180 | 120.50 ± 22.68 | 484.93 ± 125.23 | 4 |
| Compound E | 10 | 887.15 ± 221.56 | 3017.19 ± 526.52 | 3.4 |
| | 60 | 273.65 ± 101.93 | 958.56 ± 336.79 | 3.5 |
| | 180 | 84.57 ± 42.34 | 313.74 ± 56.58 | 3.7 |

It can be seen from Table 9 that Compounds A to E may be rapidly distributed to the brain after intravenous administration. The brain/blood concentration ratio reaches 1.6-3.4:1 after 10 min, and the drugs still remain at relatively high concentrations within brain and continue exerting effects after 1-3 h, which indicates that Compounds A to E have a very good brain-targeting effect. Compounds D-bornyl ferulate and D-tanshinol borneol ester may also penetrate the blood-brain barrier and reach the brain after intravenous administration, but only small amounts thereof enter the brain. The brain/blood concentration ratio is 0.52:1 and 0.47:1, respectively, after 10 min, and increases after 1 h, which indicates that compounds D-bornyl ferulate and D-tanshinol borneol ester don't have a good brain-targeting effect. However, the compounds entering the brain are slowly metabolized and still remain at relatively high drug concentrations within the brain and continue exerting effects after 3 h.

A comparison of brain/blood concentrations after intravenous injection of 4 mg/kg of phenylpropionate compounds A to E, D-bornyl ferulate, and D-tanshinol borneol ester shows that phenylpropionate compounds are more easily and rapidly distributed into the brain to exert therapeutic effects, and have more clinical significance for cerebral stroke that requires first aid.

It can be seen from the above-mentioned examples in the present disclosure that the phenylpropionate compound of the present disclosure has a short synthesis process, economical and easily available raw materials, being non-toxic and harmless, an easily controlled synthesis process, no production of harmful by-products, being an environmentally friendly and economical process, may be widely used as a medicament for treating cerebral stroke, and has a broad application prospect.

The phenylpropionate compound of the present disclosure provides an extended treatment time window, is useful as an anti-thrombus, anti-inflammatory, and cerebral stroke-treating medicament, and shows no obvious side effects.

The applicant has stated that although the phenylpropionate compound, the preparation method for the phenylpropionate compound, and the application thereof in the present disclosure are described through the embodiments described above, the present disclosure is not limited to the embodiments described above, which means that implementation of the present disclosure does not necessarily depend on the embodiments described above. It should be apparent to those skilled in the art that any improvements made to the present disclosure, equivalent replacements of raw materials selected in the present disclosure and addition of adjuvant ingredients thereof, and selections of specific methods, etc., all fall within the protection scope and the disclosed scope of the present disclosure.

The invention claimed is:

1. A phenylpropionate compound which is any one of compounds having the following Formulas A to E:

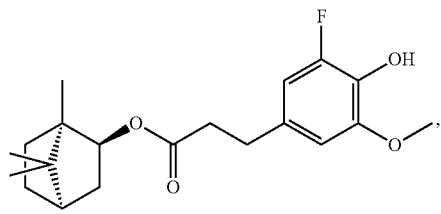

Formula A

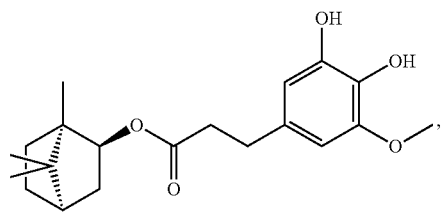

Formula B

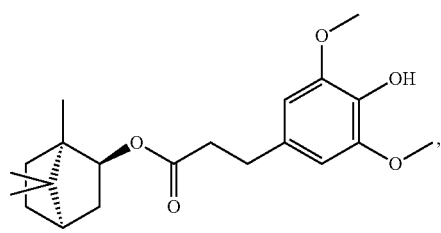

Formula C

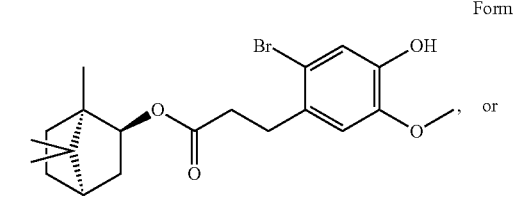

Formula D or

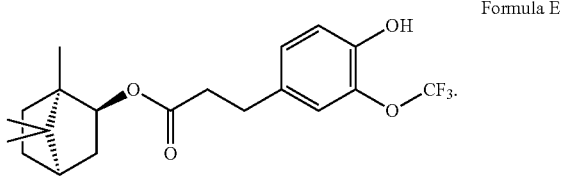

Formula E

2. A preparation method for the phenylpropionate compound of claim 1, which is:
hydrogenating a phenylacrylate compound represented by Formula IV in the presence of a catalyst to obtain a phenylpropionate compound represented by Formula I, with a reaction equation as follows:

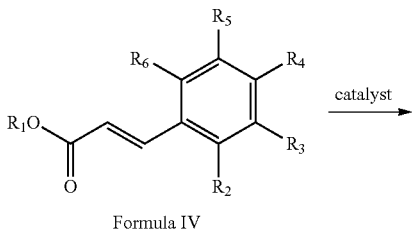

Formula IV

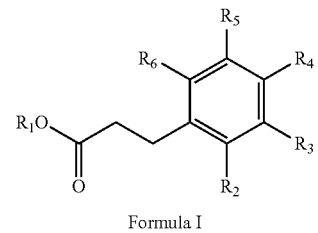

Formula I wherein $R_1$ is (1R,2S,4R)-1,7,7-trimethylbicyclo[2.2.1]heptan-2-yl or (1S,2R,4S)-1,7,7-trimethylbicyclo[2.2.1]heptan-2-yl, $R_2$ is hydrogen, $R_3$ is methoxy or trifluoromethoxy, $R_4$ is hydroxy, $R_5$ is hydrogen, fluorine, hydroxy, or methoxy, and $R_6$ is hydrogen or bromine.

3. The preparation method of claim 2, wherein a molar ratio of the phenylacrylate compound represented by Formula IV to the catalyst is 1:(0.05-1.0);
the catalyst is any one or a combination of at least two of Raney nickel, nickel boride, palladium carbon, platinum carbon, cuprous chromate, chlorotris(triphenylphosphine)rhodium, chlorohydridotris(triphenylphosphine)ruthenium, or hydridotris(triphenylphosphine)iridium;
a reductant in the hydrogenation reaction is hydrogen or ammonium formate;
a molar ratio of the reductant to the phenylacrylate compound represented by Formula IV is (15-25):1;
the hydrogenation reaction is performed at a temperature of 0 to 80° C.; and
the hydrogenation reaction is performed for 1 to 30 h.

4. The preparation method of claim 2, wherein a preparation method for the phenylacrylate compound represented by Formula IV is: reacting a malonate monoester represented by Formula II with a benzaldehyde compound represented by Formula III in the presence of a catalyst to obtain a phenylacrylate compound represented by Formula IV, with a reaction equation as follows:

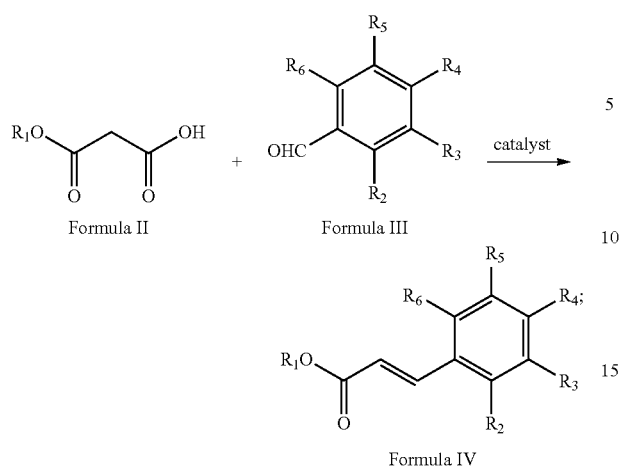

Formula II + Formula III → Formula IV wherein $R_1$ is (1R,2S,4R)-1,7,7-trimethylbicyclo[2.2.1]heptan-2-yl or (1S,2R,4S)-1,7,7-trimethylbicyclo[2.2.1]heptan-2-yl $R_2$ is hydrogen, $R_3$ is methoxy or trifluoromethoxy, $R_4$ is hydroxy, $R_5$ is hydrogen, fluorine, hydroxy, or methoxy, and $R_6$ is hydrogen or bromine.

5. The preparation method of claim 4, wherein a molar ratio of the malonate monoester represented by Formula II to the benzaldehyde compound represented by Formula III is (0.5-1.5):1;
the catalyst is any one or a combination of at least two of pyridine, piperidine, or acetic acid;
the catalyst is used in an amount of 0.1-5 times a molar amount of the substituted benzaldehyde represented by Formula III;
a solvent of the reaction is any one or a combination of at least two of toluene, xylene, benzene, DMF, n-heptane, or DMSO;
the reaction is performed at a temperature of 50 to 150° C.; and
the reaction is performed for 1 to 10 h.

6. The preparation method of claim 2, wherein a preparation method for the phenylacrylate compound represented by Formula IV is: subjecting an alcohol represented by Formula V and a phenylacrylic acid compound represented by Formula VI to a condensation reaction to obtain a phenylacrylate compound represented by Formula IV, with a reaction equation as follows:

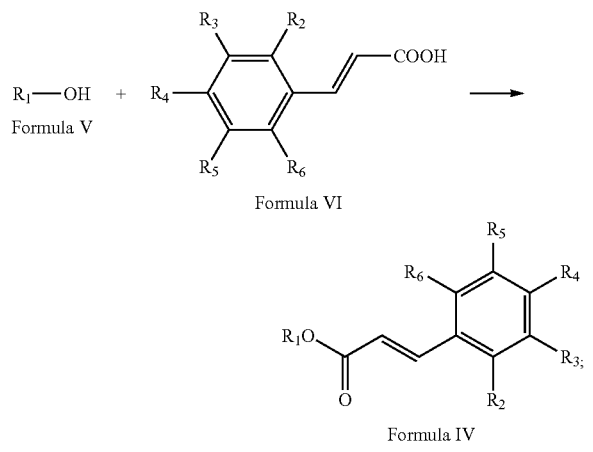

wherein $R_1$ is (1R,2S,4R)-1,7,7-trimethylbicyclo[2.2.1]heptan-2-yl or (1S,2R,4S)-1,7,7-trimethylbicyclo[2.2.1]heptan-2-yl, $R_2$ is hydrogen, $R_3$ is methoxy or trifluoromethoxy, $R_4$ is hydroxy, $R_5$ is hydrogen, fluorine, hydroxy, or methoxy, and $R_6$ is hydrogen or bromine.

7. The preparation method of claim 6, wherein a molar ratio of the alcohol represented by Formula V to the phenylacrylic acid compound represented by Formula VI is (0.5-1.5):1;
a solvent of the reaction is any one or a combination of at least two of toluene, xylene, dichloromethane, or trichloromethane;
the reaction is performed at a temperature of 15 to 80° C.; and
the reaction is performed for 3 to 30 h.

8. The preparation method of claim 2, wherein a preparation method for the phenylacrylate compound represented by Formula IV is: subjecting a compound represented by Formula VII and a benzaldehyde compound represented by Formula III to a Wittig reaction in the presence of a base to obtain a phenylacrylate compound represented by Formula IV, with a reaction equation as follows:

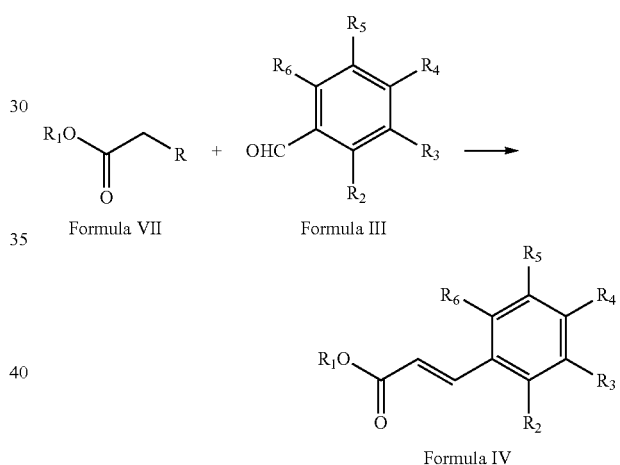

wherein $R_1$ is (1R,2S,4R)-1,7,7-trimethylbicyclo[2.2.1]heptan-2-yl or (1S,2R,4S)-1,7,7-trimethylbicyclo[2.2.1]heptan-2-yl $R_2$ is hydrogen, $R_3$ is methoxy or trifluoromethoxy, $R_4$ is hydroxy, $R_5$ is hydrogen, fluorine, hydroxy, or methoxy, and $R_6$ is hydrogen or bromine; and R is diphenyloxyphosphono, diethoxyphosphono, triphenylphosphine bromide, or triphenylphosphine chloride;
a molar ratio of the compound represented by Formula VII to the benzaldehyde compound represented by Formula III is 1:(1-1.5);
the base is any one or a combination of at least two of n-butyl lithium, potassium t-butoxide, sodium methoxide, sodium ethoxide, sodium hydride, or potassium carbonate;
the Wittig reaction is performed at a temperature of −80 to 60° C.; and
the Wittig reaction is performed for 1-12 h.

9. A pharmaceutically acceptable salt or solvate of the phenylpropionate compound of claim 1.

10. A pharmaceutical composition including the phenylpropionate compound of claim 1.

11. A method for treating cerebral stroke, comprising administering a therapeutically effective amount of a phenylpropionate compound of claim 1 to a patient in need thereof.

12. The pharmaceutically acceptable salt or solvate of claim 9, wherein the pharmaceutically acceptable salt is a lithium salt, a sodium salt, a potassium salt, or a magnesium salt.

13. The pharmaceutically acceptable salt or solvate of claim 9, wherein the solvate is a hydrate or an alcoholate.

14. The pharmaceutical composition of claim 10, wherein the pharmaceutical composition further comprises a pharmaceutically acceptable adjuvant, wherein, the pharmaceutically acceptable adjuvant is any one or a combination of at least two of an excipient, a diluent, a carrier, a flavoring agent, a binder, or a filler; and the pharmaceutical composition is in a dosage form of an oral preparation, a parenteral preparation, or a topical preparation.

* * * * *